US008759299B2

(12) United States Patent
Dong et al.

(10) Patent No.: US 8,759,299 B2
(45) Date of Patent: *Jun. 24, 2014

(54) ANALOGUES OF INSULIN-LIKE GROWTH FACTOR-1 (IGF-1) HAVING AMINO ACID SUBSTITUTION AT POSITION 59

(75) Inventors: Zheng Xin Dong, Holliston, MA (US); Nicholas C. Prairie, Franklin, MA (US); Maria L. Ufret, North Grafton, MA (US); Jundong Zhang, Newton, MA (US); Deborah M. Rothman, Arlington, MA (US); Jeanne Mary Comstock, West Boylston, MA (US)

(73) Assignee: Ipsen Pharma S.A.S., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/386,220

(22) PCT Filed: Jul. 22, 2010

(86) PCT No.: PCT/US2010/002062
§ 371 (c)(1),
(2), (4) Date: Apr. 6, 2012

(87) PCT Pub. No.: WO2011/011072
PCT Pub. Date: Jan. 27, 2011

(65) Prior Publication Data
US 2012/0190616 A1    Jul. 26, 2012

Related U.S. Application Data

(60) Provisional application No. 61/271,549, filed on Jul. 22, 2009.

(51) Int. Cl.
*A61K 38/16*      (2006.01)
*A61K 38/00*      (2006.01)

(52) U.S. Cl.
USPC .......................................... 514/21.3; 530/324

(58) Field of Classification Search
None
See application file for complete search history.

(56) References Cited

U.S. PATENT DOCUMENTS

| | | | |
|---|---|---|---|
| 4,745,179 A | | 5/1988 | Ueda et al. |
| 4,888,286 A | * | 12/1989 | Crea .......................... 435/91.52 |
| 5,654,177 A | | 8/1997 | Buell et al. |
| 5,824,642 A | | 10/1998 | Attie et al. |
| 6,310,040 B1 | | 10/2001 | Bozyczko-Coyne et al. |
| 2002/0165155 A1 | | 11/2002 | Schaffer et al. |
| 2003/0191065 A1 | | 10/2003 | Dubaquie et al. |
| 2006/0293507 A1 | | 12/2006 | Schaffer et al. |
| 2007/0032405 A1 | | 2/2007 | DeFrees |
| 2007/0032408 A1 | | 2/2007 | Holmes et al. |
| 2008/0058259 A1 | | 3/2008 | Clark |
| 2010/0173839 A1 | | 7/2010 | Glass |

FOREIGN PATENT DOCUMENTS

| | | |
|---|---|---|
| EP | 0158892 A2 | 10/1985 |
| EP | 1674113 | 6/2006 |
| WO | 85/00831 | 2/1985 |
| WO | 0040613 A1 | 7/2000 |
| WO | 2005/087797 | 9/2005 |
| WO | 2006/066891 | 6/2006 |
| WO | 2006/130769 | 12/2006 |
| WO | 2007/102686 | 9/2007 |

OTHER PUBLICATIONS

Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
Keating 2008. Biodrugs 22:177-188.*
Mohamed-Ali et al. 2002. Treat Endoc. 1:399-410.*
Frantz, (Nature Reviews Drug Discovery 2003, 2:501.*
Pettit et al 1998. Trends in Biotech. 16:343-349.*
Elliot, S. et al., "Yeast-derived recombinant human insulin-like growth factor I: production, purification, and structural characterization", J. Protein Chem., 1990, 9:95-104.
Fransson, Jonas R., Oxidation of Human Insulin-Like Growth Factor I in Formulation Studies. 3. Factorial Experiments of the Effects of Ferric Ions, EDTA, and Visible Light on Methionine Oxidation and Covalent Aggregation in Aqueous Solution, J. of Pharm. Sciences, 1997, p. 1046-1050, vol. 86, No. 9.
Loddick, Sarah A. et al., Displacement of Insulin-Like Growth Factors from their Binding Proteins as a Potential Treatment for Stroke, Proc. Natl. Acad. Sci. USA, 1998, p. 1894-1898, vol. 95.
Niwa, Mineo et al., Chemical Synthesis, Cloning, and Expression of Genes for Human Somatomedin C (Insulin-like Growth Factor I) and 59Val-Somatomedin C, Annals of the NY Academy of Sciences, 1986, p. 31-52, vol. 469.
Berneman, A. et al., "Incorporation of tritiated thymidine into DNA of rat liver: a critique of various evaluation methods", Biochimie, 1975, p. 773, vol. 57. (Abstract only).
Cascieri, M. A. et al., "Stimulation of DNA synthesis in rat A10 vascular smooth muscle cells by threonine-59 insulin-like growth factor I", Circ. Res., 1986, pp. 171-177, vol. 59.
Heck, H. D. et al., "The measurement of cell turnover rates using stable isotope-labelled thymidine: experiments on the small intestine and on a transplantable lymphatic tumour of the mouse", Cell Tissue Kinet., 1978, p. 597, vol. 11. (Abstract only).
Peters, M. A. et al., "Expression of a biologically active analogue of somatomedin-C/insulin-like growth factor I", Gene, 1985, pp. 83-89, vol. 35.
Shooter, G. K., "Insulin-like growth factor (IGF)-I A- and B-domain analogues with altered type 1 IGF and insulin receptor binding specificities", J. Mol. Endo., 1996, pp. 237-246, vol. 17.

* cited by examiner

*Primary Examiner* — Shulamith H Shafer
(74) *Attorney, Agent, or Firm* — Janice M. Klunder

(57) ABSTRACT

The present invention relates to novel analogues of insulin-like growth factor-1 (IGF-1), pharmaceutical compositions containing said analogues, and the use of said analogues for treatment of IGF-1-receptor mediated conditions, such as short stature, diabetes therapy, neurodegenerative disease treatment, and cartilage repair. More particularly, the present invention relates to novel analogues of IGF-1 having an amino acid substitution at position 59, e.g., (Asn$^{59}$)hIGF-1 (1-70)-OH (SEQ ID NO:1), and other substitution(s) as defined herein.

5 Claims, No Drawings

SEQUENCE LISTING

```
<160> NUMBER OF SEQ ID NOS: 56

<210> SEQ ID NO 1
<211> LENGTH: 70
<212> TYPE: PRT
<213> ORGANISM: Artificial Sequence
<220> FEATURE:
<223> OTHER INFORMATION: analog of IGF-1

<400> SEQUENCE: 1

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Asn Tyr Cys Ala Pro Leu
    50                  55                  60

Lys Pro Ala Lys Ser Ala
65                  70

<210> SEQ ID NO 2
<211> LENGTH: 62
<212> TYPE: PRT
<213> ORGANISM: Artificial Sequence
<220> FEATURE:
<223> OTHER INFORMATION: analog of IGF-1

<400> SEQUENCE: 2

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Asn Tyr Cys Ala
    50                  55                  60

<210> SEQ ID NO 3
<211> LENGTH: 67
<212> TYPE: PRT
<213> ORGANISM: Artificial Sequence
<220> FEATURE:
<223> OTHER INFORMATION: analog of IGF-1
```

-continued

```
<400> SEQUENCE: 3

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Arg Ala Pro Gln Thr Gly Ile Val Asp Glu Cys Cys Phe Arg Ser
        35                  40                  45

Cys Asp Leu Arg Arg Leu Glu Asn Tyr Cys Ala Pro Leu Lys Pro Ala
50                  55                  60

Lys Ser Ala
65

<210> SEQ ID NO 4
<211> LENGTH: 70
<212> TYPE: PRT
<213> ORGANISM: Artificial Sequence
<220> FEATURE:
<223> OTHER INFORMATION: analog of IGF-1

<400> SEQUENCE: 4

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Pro Lys Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Asn Tyr Cys Ala Pro Leu
50                  55                  60

Lys Pro Ala Lys Ser Ala
65                  70

<210> SEQ ID NO 5
<211> LENGTH: 62
<212> TYPE: PRT
<213> ORGANISM: Artificial Sequence
<220> FEATURE:
<223> OTHER INFORMATION: analog of IGF-1

<400> SEQUENCE: 5

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Pro Lys Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Asn Tyr Cys Ala
50                  55                  60

<210> SEQ ID NO 6
<211> LENGTH: 70
<212> TYPE: PRT
<213> ORGANISM: Artificial Sequence
<220> FEATURE:
<223> OTHER INFORMATION: analog of IGF-1

<400> SEQUENCE: 6

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30
```

```
Ser Ser Ser Arg Arg Ala Pro Gln Thr Gly Ile Val Asp Glu Cys Cys
        35                  40                  45

Phe Arg Ser Cys Ser Leu Arg Leu Glu Asn Tyr Cys Ala Pro Leu
 50                  55                  60

Lys Pro Ala Lys Ser Ala
 65                  70

<210> SEQ ID NO 7
<211> LENGTH: 71
<212> TYPE: PRT
<213> ORGANISM: Artificial Sequence
<220> FEATURE:
<223> OTHER INFORMATION: analog of IGF-1

<400> SEQUENCE: 7

Ser Gly Pro Glu Thr Leu Cys Gly Ala Glu Leu Val Asp Ala Leu Gln
 1               5                  10                  15

Phe Val Cys Gly Asp Arg Gly Phe Tyr Phe Asn Lys Pro Thr Gly Tyr
                20                  25                  30

Gly Ser Ser Ser Arg Arg Ala Pro Gln Thr Gly Ile Val Asp Glu Cys
            35                  40                  45

Cys Phe Arg Ser Cys Asp Leu Arg Arg Leu Glu Asn Tyr Cys Ala Pro
 50                  55                  60

Leu Lys Pro Ala Lys Ser Ala
 65                  70

<210> SEQ ID NO 8
<211> LENGTH: 68
<212> TYPE: PRT
<213> ORGANISM: Artificial Sequence
<220> FEATURE:
<223> OTHER INFORMATION: analog of IGF-1

<400> SEQUENCE: 8

Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Asn Tyr Cys Ala Thr Pro
 50                  55                  60

Ala Lys Ser Glu
 65

<210> SEQ ID NO 9
<211> LENGTH: 70
<212> TYPE: PRT
<213> ORGANISM: Artificial Sequence
<220> FEATURE:
<223> OTHER INFORMATION: analog of IGF-1

<400> SEQUENCE: 9

Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Tyr Arg Leu Glu Asn Tyr Cys Ala Pro Leu
 50                  55                  60
```

```
Lys Pro Ala Lys Ser Ala
 65                  70
```

<210> SEQ ID NO 10
<211> LENGTH: 70
<212> TYPE: PRT
<213> ORGANISM: Artificial Sequence
<220> FEATURE:
<223> OTHER INFORMATION: analog of IGF-1

<400> SEQUENCE: 10

```
Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
             35                  40                  45

Thr Arg Ser Cys Asp Leu Arg Arg Leu Glu Asn Tyr Cys Ala Pro Leu
         50                  55                  60

Lys Pro Ala Lys Ser Ala
 65                  70
```

<210> SEQ ID NO 11
<211> LENGTH: 70
<212> TYPE: PRT
<213> ORGANISM: Artificial Sequence
<220> FEATURE:
<223> OTHER INFORMATION: analog of IGF-1

<400> SEQUENCE: 11

```
Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
             35                  40                  45

Phe Arg Ser Cys Asp Leu Arg Arg Leu Glu Asn Tyr Cys Asn Pro Leu
         50                  55                  60

Lys Pro Ala Lys Ser Ala
 65                  70
```

<210> SEQ ID NO 12
<211> LENGTH: 70
<212> TYPE: PRT
<213> ORGANISM: Artificial Sequence
<220> FEATURE:
<223> OTHER INFORMATION: analog of IGF-1

<400> SEQUENCE: 12

```
Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
             35                  40                  45

Phe Arg Ser Cys Asp Leu Arg Arg Leu Glu Asn Phe Cys Ala Pro Leu
         50                  55                  60

Lys Pro Ala Lys Ser Ala
 65                  70
```

-continued

```
<210> SEQ ID NO 13
<211> LENGTH: 70
<212> TYPE: PRT
<213> ORGANISM: Artificial Sequence
<220> FEATURE:
<223> OTHER INFORMATION: analog of IGF-1

<400> SEQUENCE: 13

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Ser Ser Cys Asp Leu Arg Arg Leu Glu Asn Tyr Cys Ala Pro Leu
        50                  55                  60

Lys Pro Ala Lys Ser Ala
65                  70

<210> SEQ ID NO 14
<211> LENGTH: 70
<212> TYPE: PRT
<213> ORGANISM: Artificial Sequence
<220> FEATURE:
<223> OTHER INFORMATION: analog of IGF-1

<400> SEQUENCE: 14

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Gln Leu Glu Asn Tyr Cys Ala Pro Leu
        50                  55                  60

Lys Pro Ala Lys Ser Ala
65                  70

<210> SEQ ID NO 15
<211> LENGTH: 70
<212> TYPE: PRT
<213> ORGANISM: Artificial Sequence
<220> FEATURE:
<223> OTHER INFORMATION: analog of IGF-1

<400> SEQUENCE: 15

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Arg Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Leu Tyr Cys Ala Pro Leu
        50                  55                  60

Arg Pro Ala Arg Ser Ala
65                  70

<210> SEQ ID NO 16
<211> LENGTH: 70
<212> TYPE: PRT
<213> ORGANISM: Artificial Sequence
<220> FEATURE:
```

```
<223> OTHER INFORMATION: analog of IGF-1

<400> SEQUENCE: 16

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Leu Tyr Cys Ala Pro Leu
    50                  55                  60

Arg Pro Ala Arg Ser Ala
65                  70

<210> SEQ ID NO 17
<211> LENGTH: 70
<212> TYPE: PRT
<213> ORGANISM: Artificial Sequence
<220> FEATURE:
<223> OTHER INFORMATION: analog of IGF-1

<400> SEQUENCE: 17

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Leu Arg Ser Cys Asp Leu Arg Arg Leu Glu Leu Tyr Cys Ala Pro Leu
    50                  55                  60

Lys Pro Ala Lys Ser Ala
65                  70

<210> SEQ ID NO 18
<211> LENGTH: 70
<212> TYPE: PRT
<213> ORGANISM: Artificial Sequence
<220> FEATURE:
<223> OTHER INFORMATION: analog of IGF-1
<220> FEATURE:
<221> NAME/KEY: MISC_FEATURE
<222> LOCATION: (52)..(52)
<223> OTHER INFORMATION: Xaa = beta-methyl-cysteine (B-Me-Cys)

<400> SEQUENCE: 18

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Xaa Asp Leu Arg Arg Leu Glu Leu Tyr Cys Ala Pro Leu
    50                  55                  60

Lys Pro Ala Lys Ser Ala
65                  70

<210> SEQ ID NO 19
<211> LENGTH: 70
<212> TYPE: PRT
<213> ORGANISM: Artificial Sequence
<220> FEATURE:
<223> OTHER INFORMATION: analog of IGF-1
```

```
<220> FEATURE:
<221> NAME/KEY: MISC_FEATURE
<222> LOCATION: (47)..(47)
<223> OTHER INFORMATION: Xaa = beta-methyl-cysteine (B-Me-Cys)

<400> SEQUENCE: 19

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Xaa Cys
            35                  40                  45

Phe Arg Ser Cys Asp Leu Arg Arg Leu Glu Leu Tyr Cys Ala Pro Leu
        50                  55                  60

Lys Pro Ala Lys Ser Ala
65                  70

<210> SEQ ID NO 20
<211> LENGTH: 71
<212> TYPE: PRT
<213> ORGANISM: Artificial Sequence
<220> FEATURE:
<223> OTHER INFORMATION: analog of IGF-1

<400> SEQUENCE: 20

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Leu Tyr Cys Ala Pro Leu
        50                  55                  60

Lys Pro Ala Lys Ser Ala Glu
65                  70

<210> SEQ ID NO 21
<211> LENGTH: 71
<212> TYPE: PRT
<213> ORGANISM: Artificial Sequence
<220> FEATURE:
<223> OTHER INFORMATION: analog of IGF-1

<400> SEQUENCE: 21

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Leu Tyr Cys Ala Pro Leu
        50                  55                  60

Lys Pro Ala Lys Ser Ala Asp
65                  70

<210> SEQ ID NO 22
<211> LENGTH: 71
<212> TYPE: PRT
<213> ORGANISM: Artificial Sequence
<220> FEATURE:
<223> OTHER INFORMATION: analog of IGF-1
```

-continued

```
<400> SEQUENCE: 22

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Leu Tyr Cys Ala Pro Leu
    50                  55                  60

Lys Pro Ala Lys Ser Ala Lys
65                  70

<210> SEQ ID NO 23
<211> LENGTH: 71
<212> TYPE: PRT
<213> ORGANISM: Artificial Sequence
<220> FEATURE:
<223> OTHER INFORMATION: analog of IGF-1

<400> SEQUENCE: 23

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Leu Tyr Cys Ala Pro Leu
    50                  55                  60

Lys Pro Ala Lys Ser Ala Ser
65                  70

<210> SEQ ID NO 24
<211> LENGTH: 70
<212> TYPE: PRT
<213> ORGANISM: Artificial Sequence
<220> FEATURE:
<223> OTHER INFORMATION: analog of IGF-1

<400> SEQUENCE: 24

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Leu Tyr Cys Ala Pro Leu
    50                  55                  60

Lys Pro Ala Lys Thr Ala
65                  70

<210> SEQ ID NO 25
<211> LENGTH: 70
<212> TYPE: PRT
<213> ORGANISM: Artificial Sequence
<220> FEATURE:
<223> OTHER INFORMATION: analog of IGF-1

<400> SEQUENCE: 25

Gly Pro Glu Thr Leu Cys Gly Ala Glu Leu Val Asp Ala Leu Gln Phe
1               5                   10                  15
```

```
Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
            35                  40                  45

Phe Arg Thr Cys Asp Leu Arg Arg Leu Glu Leu Tyr Cys Ala Pro Leu
50                  55                  60

Lys Pro Ala Lys Ser Ala
65                  70

<210> SEQ ID NO 26
<211> LENGTH: 70
<212> TYPE: PRT
<213> ORGANISM: Artificial Sequence
<220> FEATURE:
<223> OTHER INFORMATION: analog of IGF-1
<220> FEATURE:
<221> NAME/KEY: MISC_FEATURE
<222> LOCATION: (47)..(47)
<223> OTHER INFORMATION: Xaa = N-methyl-cysteine (N-Me-Cys)
<220> FEATURE:
<221> NAME/KEY: MISC_FEATURE
<222> LOCATION: (59)..(59)
<223> OTHER INFORMATION: Xaa = norleucine (Nle)

<400> SEQUENCE: 26

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Xaa Cys
            35                  40                  45

Phe Arg Ser Cys Asp Leu Arg Arg Leu Glu Xaa Tyr Cys Ala Pro Leu
50                  55                  60

Lys Pro Ala Lys Ser Ala
65                  70

<210> SEQ ID NO 27
<211> LENGTH: 70
<212> TYPE: PRT
<213> ORGANISM: Artificial Sequence
<220> FEATURE:
<223> OTHER INFORMATION: analog of IGF-1
<220> FEATURE:
<221> NAME/KEY: MISC_FEATURE
<222> LOCATION: (59)..(59)
<223> OTHER INFORMATION: Xaa = norleucine (Nle)
<220> FEATURE:
<221> NAME/KEY: MISC_FEATURE
<222> LOCATION: (69)..(69)
<223> OTHER INFORMATION: Xaa = alpha-aminoisobutyric acid (Aib)

<400> SEQUENCE: 27

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Xaa Tyr Cys Ala Pro Leu
50                  55                  60

Lys Pro Ala Lys Xaa Ala
65                  70

<210> SEQ ID NO 28
```

```
<211> LENGTH: 70
<212> TYPE: PRT
<213> ORGANISM: Artificial Sequence
<220> FEATURE:
<223> OTHER INFORMATION: analog of IGF-1
<220> FEATURE:
<221> NAME/KEY: MISC_FEATURE
<222> LOCATION: (48)..(48)
<223> OTHER INFORMATION: Xaa = N-methyl-cysteine (N-Me-Cys)
<220> FEATURE:
<221> NAME/KEY: MISC_FEATURE
<222> LOCATION: (59)..(59)
<223> OTHER INFORMATION: Xaa = norleucine (Nle)

<400> SEQUENCE: 28

Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Xaa
            35                  40                  45

Phe Arg Ser Cys Asp Leu Arg Arg Leu Glu Xaa Tyr Cys Ala Pro Leu
    50                  55                  60

Lys Pro Ala Lys Ser Ala
65                  70

<210> SEQ ID NO 29
<211> LENGTH: 70
<212> TYPE: PRT
<213> ORGANISM: Artificial Sequence
<220> FEATURE:
<223> OTHER INFORMATION: analog of IGF-1
<220> FEATURE:
<221> NAME/KEY: MISC_FEATURE
<222> LOCATION: (59)..(59)
<223> OTHER INFORMATION: Xaa = norleucine (Nle)
<220> FEATURE:
<221> NAME/KEY: MISC_FEATURE
<222> LOCATION: (67)..(67)
<223> OTHER INFORMATION: Xaa = alpha-aminoisobutyric acid (Aib)

<400> SEQUENCE: 29

Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Xaa Tyr Cys Ala Pro Leu
    50                  55                  60

Lys Pro Xaa Lys Ser Ala
65                  70

<210> SEQ ID NO 30
<211> LENGTH: 70
<212> TYPE: PRT
<213> ORGANISM: Artificial Sequence
<220> FEATURE:
<223> OTHER INFORMATION: analog of IGF-1
<220> FEATURE:
<221> NAME/KEY: MISC_FEATURE
<222> LOCATION: (52)..(52)
<223> OTHER INFORMATION: Xaa = homo-cysteine (hCys)
<220> FEATURE:
<221> NAME/KEY: MISC_FEATURE
<222> LOCATION: (59)..(59)
<223> OTHER INFORMATION: Xaa = norleucine (Nle)
```

-continued

```
<400> SEQUENCE: 30

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Xaa Asp Leu Arg Arg Leu Glu Xaa Tyr Cys Ala Pro Leu
    50                  55                  60

Lys Pro Ala Lys Ser Ala
65                  70

<210> SEQ ID NO 31
<211> LENGTH: 70
<212> TYPE: PRT
<213> ORGANISM: Artificial Sequence
<220> FEATURE:
<223> OTHER INFORMATION: analog of IGF-1
<220> FEATURE:
<221> NAME/KEY: MISC_FEATURE
<222> LOCATION: (51)..(51)
<223> OTHER INFORMATION: Xaa = alpha-aminoisobutyric acid (Aib)
<220> FEATURE:
<221> NAME/KEY: MISC_FEATURE
<222> LOCATION: (59)..(59)
<223> OTHER INFORMATION: Xaa = norleucine (Nle)

<400> SEQUENCE: 31

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Xaa Cys Asp Leu Arg Arg Leu Glu Xaa Tyr Cys Ala Pro Leu
    50                  55                  60

Lys Pro Ala Lys Ser Ala
65                  70

<210> SEQ ID NO 32
<211> LENGTH: 70
<212> TYPE: PRT
<213> ORGANISM: Artificial Sequence
<220> FEATURE:
<223> OTHER INFORMATION: analog of IGF-1
<220> FEATURE:
<221> NAME/KEY: MISC_FEATURE
<222> LOCATION: (52)..(52)
<223> OTHER INFORMATION: Xaa = penicillamine (Pen)
<220> FEATURE:
<221> NAME/KEY: MISC_FEATURE
<222> LOCATION: (59)..(59)
<223> OTHER INFORMATION: Xaa = norleucine (Nle)

<400> SEQUENCE: 32

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Xaa Asp Leu Arg Arg Leu Glu Xaa Tyr Cys Ala Pro Leu
    50                  55                  60
```

```
Lys Pro Ala Lys Ser Ala
65                  70

<210> SEQ ID NO 33
<211> LENGTH: 70
<212> TYPE: PRT
<213> ORGANISM: Artificial Sequence
<220> FEATURE:
<223> OTHER INFORMATION: analog of IGF-1
<220> FEATURE:
<221> NAME/KEY: MISC_FEATURE
<222> LOCATION: (59)..(59)
<223> OTHER INFORMATION: Xaa = norleucine (Nle)
<220> FEATURE:
<221> NAME/KEY: MISC_FEATURE
<222> LOCATION: (61)..(61)
<223> OTHER INFORMATION: Xaa = penicillamine (Pen)

<400> SEQUENCE: 33

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Xaa Tyr Xaa Ala Pro Leu
    50                  55                  60

Lys Pro Ala Lys Ser Ala
65                  70

<210> SEQ ID NO 34
<211> LENGTH: 70
<212> TYPE: PRT
<213> ORGANISM: Artificial Sequence
<220> FEATURE:
<223> OTHER INFORMATION: analog of IGF-1
<220> FEATURE:
<221> NAME/KEY: MISC_FEATURE
<222> LOCATION: (54)..(54)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (59)..(59)
<223> OTHER INFORMATION: Xaa = norleucine (Nle)

<400> SEQUENCE: 34

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Xaa Arg Arg Leu Glu Xaa Tyr Cys Ala Pro Leu
    50                  55                  60

Lys Pro Ala Lys Ser Ala
65                  70

<210> SEQ ID NO 35
<211> LENGTH: 70
<212> TYPE: PRT
<213> ORGANISM: Artificial Sequence
<220> FEATURE:
<223> OTHER INFORMATION: analog of IGF-1

<400> SEQUENCE: 35
```

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Arg Leu Arg Arg Leu Glu Ile Tyr Cys Ala Pro Leu
    50                  55                  60

Lys Pro Ala Lys Ser Ala
65                  70

<210> SEQ ID NO 36
<211> LENGTH: 70
<212> TYPE: PRT
<213> ORGANISM: Artificial Sequence
<220> FEATURE:
<223> OTHER INFORMATION: analog of IGF-1

<400> SEQUENCE: 36

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Arg Arg Ser Cys Asp Leu Arg Arg Leu Glu Ile Tyr Cys Ala Pro Leu
    50                  55                  60

Lys Pro Ala Lys Ser Ala
65                  70

<210> SEQ ID NO 37
<211> LENGTH: 70
<212> TYPE: PRT
<213> ORGANISM: Artificial Sequence
<220> FEATURE:
<223> OTHER INFORMATION: analog of IGF-1

<400> SEQUENCE: 37

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Arg Cys Asp Leu Arg Arg Leu Glu Ile Tyr Cys Ala Pro Leu
    50                  55                  60

Lys Pro Ala Lys Ser Ala
65                  70

<210> SEQ ID NO 38
<211> LENGTH: 70
<212> TYPE: PRT
<213> ORGANISM: Artificial Sequence
<220> FEATURE:
<223> OTHER INFORMATION: analog of IGF-1

<400> SEQUENCE: 38

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

```
Ser Ser Ser Arg Arg Ala Pro Gln Thr Gly Ile Val Asp Glu Cys Cys
        35                  40                  45

Phe Arg Ser Cys Asp Leu Arg Arg Leu Arg Ile Tyr Cys Ala Pro Leu
    50                  55                  60

Lys Pro Ala Lys Ser Ala
65                  70

<210> SEQ ID NO 39
<211> LENGTH: 70
<212> TYPE: PRT
<213> ORGANISM: Artificial Sequence
<220> FEATURE:
<223> OTHER INFORMATION: analog of IGF-1
<220> FEATURE:
<221> NAME/KEY: MISC_FEATURE
<222> LOCATION: (59)..(59)
<223> OTHER INFORMATION: Xaa = 1-amino-1-cyclohexanecarboxylic acid
      (A6c)

<400> SEQUENCE: 39

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Xaa Tyr Cys Ala Pro Leu
    50                  55                  60

Lys Pro Ala Lys Ser Ala
65                  70

<210> SEQ ID NO 40
<211> LENGTH: 70
<212> TYPE: PRT
<213> ORGANISM: Artificial Sequence
<220> FEATURE:
<223> OTHER INFORMATION: analog of IGF-1

<400> SEQUENCE: 40

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Asp Tyr Cys Ala Pro Leu
    50                  55                  60

Lys Pro Ala Lys Ser Ala
65                  70

<210> SEQ ID NO 41
<211> LENGTH: 70
<212> TYPE: PRT
<213> ORGANISM: Artificial Sequence
<220> FEATURE:
<223> OTHER INFORMATION: analog of IGF-1

<400> SEQUENCE: 41

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30
```

```
Ser Ser Ser Arg Arg Ala Pro Gln Thr Gly Ile Val Asp Glu Cys Cys
            35                  40                  45

Phe Arg Ser Cys Asp Leu Arg Arg Leu Glu Trp Tyr Cys Ala Pro Leu
         50                  55                  60

Lys Pro Ala Lys Ser Ala
65                  70

<210> SEQ ID NO 42
<211> LENGTH: 70
<212> TYPE: PRT
<213> ORGANISM: Artificial Sequence
<220> FEATURE:
<223> OTHER INFORMATION: analog of IGF-1

<400> SEQUENCE: 42

Gly Pro Glu Thr Leu Cys Gly Ala Glu Leu Val Asp Ala Leu Gln Phe
1               5                  10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Ser Tyr Cys Ala Pro Leu
         50                  55                  60

Lys Pro Ala Lys Ser Ala
65                  70

<210> SEQ ID NO 43
<211> LENGTH: 70
<212> TYPE: PRT
<213> ORGANISM: Artificial Sequence
<220> FEATURE:
<223> OTHER INFORMATION: analog of IGF-1

<400> SEQUENCE: 43

Gly Pro Glu Thr Leu Cys Gly Ala Glu Leu Val Asp Ala Leu Gln Phe
1               5                  10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Tyr Tyr Cys Ala Pro Leu
         50                  55                  60

Lys Pro Ala Lys Ser Ala
65                  70

<210> SEQ ID NO 44
<211> LENGTH: 70
<212> TYPE: PRT
<213> ORGANISM: Artificial Sequence
<220> FEATURE:
<223> OTHER INFORMATION: analog of IGF-1

<400> SEQUENCE: 44

Gly Pro Glu Thr Leu Cys Gly Ala Glu Leu Val Asp Ala Leu Gln Phe
1               5                  10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Glu Tyr Cys Ala Pro Leu
```

```
                    50                  55                  60
Lys Pro Ala Lys Ser Ala
 65                 70

<210> SEQ ID NO 45
<211> LENGTH: 70
<212> TYPE: PRT
<213> ORGANISM: Artificial Sequence
<220> FEATURE:
<223> OTHER INFORMATION: analog of IGF-1

<400> SEQUENCE: 45

Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Gln Tyr Cys Ala Pro Leu
        50                  55                  60

Lys Pro Ala Lys Ser Ala
 65                 70

<210> SEQ ID NO 46
<211> LENGTH: 70
<212> TYPE: PRT
<213> ORGANISM: Artificial Sequence
<220> FEATURE:
<223> OTHER INFORMATION: analog of IGF-1

<400> SEQUENCE: 46

Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Arg Tyr Cys Ala Pro Leu
        50                  55                  60

Lys Pro Ala Lys Ser Ala
 65                 70

<210> SEQ ID NO 47
<211> LENGTH: 71
<212> TYPE: PRT
<213> ORGANISM: Artificial Sequence
<220> FEATURE:
<223> OTHER INFORMATION: analog of IGF-1

<400> SEQUENCE: 47

Met Gly Pro Glu Thr Leu Cys Gly Ala Glu Leu Val Asp Ala Leu Gln
 1               5                  10                  15

Phe Val Cys Gly Asp Arg Gly Phe Tyr Phe Asn Lys Pro Thr Gly Tyr
                20                  25                  30

Gly Ser Ser Ser Arg Arg Ala Pro Gln Thr Gly Ile Val Asp Glu Cys
            35                  40                  45

Cys Phe Arg Ser Cys Asp Leu Arg Arg Leu Glu Asn Tyr Cys Ala Pro
        50                  55                  60

Leu Lys Pro Ala Lys Ser Ala
 65                 70
```

-continued

<210> SEQ ID NO 48
<211> LENGTH: 65
<212> TYPE: PRT
<213> ORGANISM: Artificial Sequence
<220> FEATURE:
<223> OTHER INFORMATION: analog of IGF-1

<400> SEQUENCE: 48

```
Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Arg Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys
65
```

<210> SEQ ID NO 49
<211> LENGTH: 70
<212> TYPE: PRT
<213> ORGANISM: Homo sapiens
<220> FEATURE:
<221> NAME/KEY: MOD_RES
<222> LOCATION: (70)..(70)
<223> OTHER INFORMATION: AMIDATION

<400> SEQUENCE: 49

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70
```

<210> SEQ ID NO 50
<211> LENGTH: 70
<212> TYPE: PRT
<213> ORGANISM: Homo sapiens

<400> SEQUENCE: 50

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70
```

<210> SEQ ID NO 51
<211> LENGTH: 23
<212> TYPE: PRT
<213> ORGANISM: Artificial Sequence

```
<220> FEATURE:
<223> OTHER INFORMATION: analog of IGF-1

<400> SEQUENCE: 51

Cys Phe Arg Ser Cys Asp Leu Arg Gln Leu Glu Asn Tyr Cys Ala Pro
1               5                   10                  15

Leu Lys Pro Ala Lys Ser Ala
            20

<210> SEQ ID NO 52
<211> LENGTH: 48
<212> TYPE: PRT
<213> ORGANISM: Artificial Sequence
<220> FEATURE:
<223> OTHER INFORMATION: analog of IGF-1
<220> FEATURE:
<221> NAME/KEY: MOD_RES
<222> LOCATION: (48)..(48)
<223> OTHER INFORMATION: modified with thioester-propionyl group
<220> FEATURE:
<221> NAME/KEY: MOD_RES
<222> LOCATION: (48)..(48)
<223> OTHER INFORMATION: AMIDATION

<400> SEQUENCE: 52

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Leu
        35                  40                  45

<210> SEQ ID NO 53
<211> LENGTH: 70
<212> TYPE: PRT
<213> ORGANISM: Artificial Sequence
<220> FEATURE:
<223> OTHER INFORMATION: analog of IGF-1
<220> FEATURE:
<221> NAME/KEY: MOD_RES
<222> LOCATION: (1)..(1)
<223> OTHER INFORMATION: glyoxylyated

<400> SEQUENCE: 53

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Asn Tyr Cys Ala Pro Leu
    50                  55                  60

Lys Pro Ala Lys Ser Ala
65                  70

<210> SEQ ID NO 54
<211> LENGTH: 47
<212> TYPE: PRT
<213> ORGANISM: Artificial Sequence
<220> FEATURE:
<223> OTHER INFORMATION: analog of IGF-1
<220> FEATURE:
<221> NAME/KEY: MOD_RES
<222> LOCATION: (46)..(47)
<223> OTHER INFORMATION: thioester-propionyl linker
<220> FEATURE:
<221> NAME/KEY: MOD_RES
```

```
<222> LOCATION: (47)..(47)
<223> OTHER INFORMATION: AMIDATION

<400> SEQUENCE: 54

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Leu
            35                  40                  45

<210> SEQ ID NO 55
<211> LENGTH: 24
<212> TYPE: PRT
<213> ORGANISM: Artificial Sequence
<220> FEATURE:
<223> OTHER INFORMATION: analog of IGF-1
<220> FEATURE:
<221> NAME/KEY: MISC_FEATURE
<222> LOCATION: (1)..(1)
<223> OTHER INFORMATION: Xaa = beta-methyl-cysteine (B-Me-Cys)

<400> SEQUENCE: 55

Xaa Cys Phe Arg Ser Cys Asp Leu Arg Arg Leu Glu Leu Tyr Cys Ala
1               5                   10                  15

Pro Leu Lys Pro Ala Lys Ser Ala
                20

<210> SEQ ID NO 56
<211> LENGTH: 23
<212> TYPE: PRT
<213> ORGANISM: Artificial Sequence
<220> FEATURE:
<223> OTHER INFORMATION: analog of IGF-1
<220> FEATURE:
<221> NAME/KEY: MISC_FEATURE
<222> LOCATION: (1)..(1)
<223> OTHER INFORMATION: Xaa = N-methyl-cysteine (N-Me-Cys)
<220> FEATURE:
<221> NAME/KEY: MISC_FEATURE
<222> LOCATION: (12)..(12)
<223> OTHER INFORMATION: Xaa = norleucine (Nle)

<400> SEQUENCE: 56

Xaa Phe Arg Ser Cys Asp Leu Arg Arg Leu Glu Xaa Tyr Cys Ala Pro
1               5                   10                  15

Leu Lys Pro Ala Lys Ser Ala
                20
```

1

ANALOGUES OF INSULIN-LIKE GROWTH FACTOR-1 (IGF-1) HAVING AMINO ACID SUBSTITUTION AT POSITION 59

This application is a United States national stage filing under 35 U.S.C. §371 of international (PCT) application number PCT/US2010/002062 filed Jul. 22, 2010, and designating the US, which claims priority to U.S. provisional application No. 61/271,549 filed Jul. 22, 2009.

FIELD OF THE INVENTION

The present invention relates to novel analogues of insulin-like growth factor-1 (IGF-1), pharmaceutical compositions containing said analogues, and the use of said analogues for treatment of IGF-1-receptor mediated conditions, such as short stature, diabetes therapy, neurodegenerative disease treatment, and cartilage repair. More particularly, the present invention relates to novel analogues of IGF-1 having an amino acid substitution at position 59, e.g., (Asn$^{59}$)hIGF-1 (1-70)-OH, and other substitution(s) as defined herein.

BACKGROUND ART

IGF-1 is a 70-amino-acid polypeptide hormone having insulin-like and mitogenic growth biological activities. This hormone enhances growth of cells in a variety of tissues including musculoskeletal systems, liver, kidney, intestines, nervous system tissues, heart, and lung.

The wild-type IGF-1 has the following amino acid sequence with three intrachain disulfide bridges wherein the side-chains of residue pairs $A^6$ and $A^{48}$, $A^{47}$ and $A^{52}$, and $A^{18}$ and $A^{61}$, each form a disulfide bond (SEQ ID NO:50):

sclerosis (ALS)), muscular dystrophy and multiple sclerosis, cartilage disorders such as osteoarthritis, bone diseases such as osteoporosis, inflammatory disorders such as rheumatoid arthritis, ischemic injuries to organs such as to the heart, brain, or liver, and so forth.

As is well known to those skilled in the art, the known and potential uses of IGF-1 are varied and multitudinous. For example, a number of studies report on the use of IGF-1 as a potential therapeutic agent for treatment of neurodegenerative conditions. See, e.g., Kanje et al., *Brain Res.*, 486:396-398 (1989); Hantai et al., *J. Neurol. Sci.*, 129:122-126 (1995); Contreras et al., *Pharmac. Exp. Therap.*, 274:1443-1499 (1995); Di Giulio et al., *Society for Neuroscience*, 22:1960 (1996); Di Giulio et al., *Society for Neuroscience*, 23:894 (1997); Hsu et al., *Biochem. Mol. Med.*, 60(2):142-148 (1997); Gorio et al., *Neuroscience*, 82:1029-1037 (1998). IGF-1 therapy has been indicated in numerous neurological conditions, including ALS, stroke, epilepsy, Parkinson's disease, Alzheimer's disease, acute traumatic injury and other disorders associated with trauma, aging, disease, or injury. See, e.g., U.S. Pat. Nos. 5,093,137; 5,652,214; 5,703,045; International Publication Nos. WO 90/1483 and WO 93/02695.

Use of IGF-1 therapy for a variety of other conditions has been referred to in a number of publications. See, e.g., Schalch et al., "Modern Concepts of Insulin-Like Growth Factors," ed. Spencer (Elsevier, N.Y.), pp. 705-714 (1991); Clemmons and Underwood, *J. Clin. Endocrinol. Metab.*, 79(1):4-6 (1994); and Langford et al., *Eur. J. Clin. Invest.*, 23(9):503-516 (1993) (referring to, e.g., insulin-resistant states and diabetes); and O'Shea et al., *Am. J. Physiol.*, 264: F917-F922 (1993) (referring to, e.g., reduced renal function).

```
Gly-Pro-Glu-Thr-Leu-Cys-Gly-Ala-Glu-Leu-Val-Asp-Ala-Leu-Gln-Phe-Val-Cys-
1               5                   10                  15

Gly-Asp-Arg-Gly-Phe-Tyr-Phe-Asn-Lys-Pro-Thr-Gly-Tyr-Gly-Ser-Ser-Ser-Arg-
        20                  25                  30                  35

Arg-Ala-Pro-Gln-Thr-Gly-Ile-Val-Asp-Glu-Cys-Cys-Phe-Arg-Ser-Cys-Asp-Leu-
            40                  45                  50

Arg-Arg-Leu-Glu-Met-Tyr-Cys-Ala-Pro-Leu-Lys-Pro-Ala-Lys-Ser-Ala
55                  60                  65                  70
```

While IGF-1 is present in a wide variety of body tissues, it is normally found in an inactive form in which it is bound to an IGF binding protein (IGFBP). Six related IGFBPs are known and have been designated IGFBP1-IGFBP6. See, e.g., Holly and Martin, "Insulin-like Growth Factor Binding Proteins: A Review of Methodological Aspects of Their Purification, Analysis and Regulation," *Growth Regul.*, 4(Suppl 1):20-30 (1994). IGFBPs play an important role in IGF-1 regulation by exerting inhibitory and/or stimulatory effects on IGF-1 action. For example, about 90% of circulating IGF-1 is present in a trimolecular complex containing IGFBP-3 and acid labile submit. The IGF-1 within such complexes is unable to bind to surface receptors, and is therefore biologically inactive. IGF-1 present within the trimolecular complex also has a substantially longer half-life than uncomplexed IGF-1.

Disruption of IGF-1 action may contribute to a number of physiological disorders including neurodegenerative disorders such as motor neuron disease (i.e., amyotrophic lateral Also see U.S. Pat. No. 7,258,864 (referring to short stature); U.S. Pat. Nos. 5,110,604 and 5,427,778 (referring to, e.g., wound healing); U.S. Pat. No. 5,126,324 (referring to, e.g., cardiac disorders and growth retardation); U.S. Pat. No. 5,368,858 (referring to, e.g., defects or lesions in cartilage); U.S. Pat. Nos. 5,543,441 and 5,550,188 (referring to, e.g., tissue augmentation); U.S. Pat. No. 5,686,425 (referring to, e.g., scar tissue, localized muscular dysfunction, and urinary incontinence); and U.S. Pat. No. 5,656,598 (referring to, e.g., bone growth). Also see International Publication Nos. WO 91/12018 (referring to, e.g., intestinal disorders); WO 92/09301 and WO 92/14480 (referring to, e.g., wound healing); WO 93/08828 (referring to, e.g., neuronal damage associated with ischemia, hypoxia, or neurodegeneration); WO 94/16722 (referring to, e.g., insulin resistance); WO 96/02565A1 (referring to, e.g., IGF/IGFBP complex for promoting bone formation and for regulating bone remodeling); U.S. Patent Application Publication No. 2003/0100505 (referring to, e.g., osteoporosis); and U.S. Patent Application Publication No. 2005/0043240 (referring to obesity).

Although IGF-1 therapy has been used for a number of physiological indications, results have sometimes been unpredictable. Short-term beneficial effects sometimes do not persist (see, e.g., Miller et al., *Kidney International*, 46:201-207 (1994)) and undesirable side effects can result, particularly from administration of high doses and/or long-term administration (see, e.g., Jabri et al., *Diabetes*, 43:369-374 (1994); Wilton, *Acta Paediatr.*, 393:137-141 (1992)). Also, high levels of IGF-1 have been reported to increase risk for prostate cancer (Chan et al., *Science*, 278:563-566 (1998)).

Accordingly, there is a need in the art for better ways to treat conditions responsive to IGF-1 and/or other proteins that bind to insulin-like growth factor binding proteins. The present invention fulfills these needs and further provides other related advantages.

SUMMARY OF THE INVENTION

As discovered by the inventors of the present invention, by replacing the methionine residue at position 59 of the wild-type IGF-1 which is chemically unstable and can be easily oxidized with other amino acid as described herein, e.g., $(Asn^{59})hIGF-1(1-70)$-OH, the resulting analogues of IGF-1 are chemically more stable and as such are less susceptible to oxidation during production, purification, storage, etc.

In one aspect, the present invention is directed to peptide variants (i.e., analogues) of IGF-1 of the following formula (I),

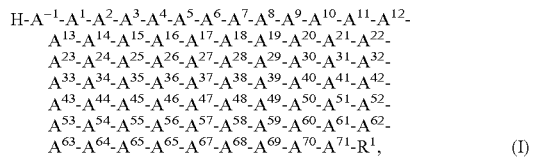

wherein:
$A^{-1}$ is Met, Ser, or deleted;
$A^1$ is Gly, Ala, Asn, Asp, Gln, Glu, or deleted;
$A^2$ is Pro, Ala, Arg, Asp, Gln, Glu, Lys, or deleted;
$A^3$ is Glu, Ala, Asp, Gln, or deleted;
$A^4$ is Thr, Ala, Asn, Asp, Gln, Glu, Ser;
$A^5$ is Leu, Ace, Ala, Ile, or Val;
$A^6$ is Cys, D-Cys, hCys, D-hCys, β-Me-Cys, N-Me-Cys, D-N-Me-Cys, Ala, Pen, or D-Pen;
$A^7$ is Gly, Ala, Asn, Asp, Gln or Glu;
$A^8$ is Ala, Arg, Asn, Asp, Gln, Glu, or Lys;
$A^9$ is Glu, Ala, Asp, or Gln;
$A^{10}$ is Leu, Acc, Ala, Ile, or Val;
$A^{11}$ is Val, Ala, Ile, or Leu;
$A^{12}$ is Asp, Ala, Arg, Asn, Gln, Glu, or Lys;
$A^{13}$ is Ala, Asn, Asp, Gln, Glu, Ile, Leu, or Val;
$A^{14}$ is Leu, Acc, Ala, Ile, or Val;
$A^{15}$ is Gln, Ala, Asn, Asp, or Glu;
$A^{16}$ is Phe, Ala, Asn, Asp, Gln, Glu, Trp, or Tyr;
$A^{17}$ is Val, Ala, Ile or Leu;
$A^{18}$ is Cys, D-Cys, hCys, D-hCys, β-Me-Cys, D-β-Me-Cys, N-Me-Cys, D-N-Me-Cys, Ala, Pen, or D-Pen;
$A^{19}$ is Gly, Ala, Asn, Asp, Gln, or Glu;
$A^{20}$ is Asp, Ala, Asn, Gln, or Glu;
$A^{21}$ is Arg, Ala, Asn, Asp, Gln, Glu, or Lys;
$A^{22}$ is Gly, Ala, Asn, Asp, Gln, or Glu;
$A^{23}$ is Phe, Ala, Trp, or Tyr;
$A^{24}$ is Tyr, Ala, Phe, or Trp;
$A^{25}$ is Phe, Ala, Trp, or Tyr;
$A^{26}$ is Asn, Ala, Asp, Gln, Glu, Ser, or Thr;
$A^{27}$ is Lys, Ala, Arg, Asn, Asp, Gln, Glu, or Pro;
$A^{28}$ is Pro, Ala, Arg, or Lys;
$A^{29}$ is Thr, Ala, Asn, Asp, Gln, Glu, or Ser;
$A^{30}$ is Gly, Ala, Asn, Asp, Gln, or Glu;
$A^{31}$ is Tyr, Ala, Phe, or Trp;
$A^{32}$ is Gly, Ala, Asn, Asp, Gln, or Glu;
$A^{33}$ is Ser, Ala, Thr, or Val;
$A^{34}$ is Ser, Ala, Asn, Asp, Gln, Glu, or Thr;
$A^{35}$ is Ser, Ala, Asn, Asp, Gln, Glu, or Thr;
$A^{36}$ is Arg, Ala, Asn, Asp, Gln, Glu, or Lys;
$A^{37}$ is Arg, Ala, Asn, Asp, Gln, Glu, or Lys;
$A^{38}$ is Ala, Asn, Asp, Gln, or Glu;
$A^{39}$ is Pro, Ala, Arg, or Glu;
$A^{40}$ is Gln, Ala, Asn, Asp, or Glu;
$A^{41}$ is Thr, Ala, Asn, Asp, Gln, Glu, or Ser;
$A^{42}$ is Gly, Ala, Arg, Asn, Asp, Gln, Glu, or Lys;
$A^{43}$ is Ile, Ala, Arg, Asn, Asp, Gln, Glu, or Lys;
$A^{44}$ is Val, Ala, Arg, Asn, Asp, Gln, Glu, Ile, Leu, or Lys;
$A^{45}$ is Asp, Ala, Arg, Asn, Gln, Glu, or Lys;
$A^{46}$ is Glu, Ala, Arg, Asn, Asp, Gln, or Lys;
$A^{47}$ is Cys, D-Cys, hCys, D-hCys, β-Me-Cys, D-β-Me-Cys, N-Me-Cys, D-N-Me-Cys, Ala, Pen, or D-Pen;
$A^{48}$ is Cys, D-Cys, hCys, D-hCys, β-Me-Cys, D-β-Me-Cys, N-Me-Cys, D-N-Me-Cys, Ala, Pen, or D-Pen;
$A^{49}$ is Phe, Ala, Arg, Ile, Leu, Lys, Ser, Thr, Trp, Tyr, or Val;
$A^{50}$ is Arg, Ala, Lys, Ser, or Thr;
$A^{51}$ is Ser, Aib, Ala, Arg, Lys, or Thr;
$A^{52}$ is Cys, D-Cys, hCys, D-hCys, β-Me-Cys, D-β-Me-Cys, N-Me-Cys, D-N-Me-Cys, Ala, Pen, or D-Pen;
$A^{53}$ is Asp, Ala, Arg, Asn, Gln, Glu, Lys, Ser, or Thr;
$A^{54}$ is Leu, Acc, Ala, Ile, or Val;
$A^{55}$ is Arg, Ala, Ile, Leu, Lys, Phe, Trp, Tyr, or Val;
$A^{56}$ is Arg, Ala, Asn, Asp, Gln, Glu, or Lys;
$A^{57}$ is Leu, Acc, Ala, Ile, or Val;
$A^{58}$ is Glu, Acc, Ala, Arg, Asn, Asp, Gln, or Lys;
$A^{59}$ is Acc, Ala, Arg, Asn, Asp, Gln, Glu, Ile, Leu, Lys, Nle, Ser, D-Ser, Thr, Trp, Tyr, or Val;
$A^{60}$ is Tyr, Ala, Phe, or Trp;
$A^{61}$ is Cys, D-Cys, hCys, D-hCys, β-Me-Cys, D-β-Me-Cys, N-Me-Cys, D-N-Me-Cys, Ala, Pen, or D-Pen;
$A^{62}$ is Ala, Asn, Asp, Gln, Glu, Ile, Leu, or Val;
$A^{63}$ is Pro, D-Pro, Ala, Ser, Thr, or deleted;
$A^{64}$ is Leu, D-Leu, des-Leu, Ala, Ile, Val, or deleted;
$A^{65}$ is Lys, D-Lys, des-Lys, Ala, Arg, Ile, Leu, Val, or deleted;
$A^{66}$ is Pro, D-Pro, Ala, or deleted;
$A^{67}$ is Ala, D-Ala, Aib, or deleted;
$A^{68}$ is Lys, D-Lys, Ala, Arg, Ile, Leu, Val, or deleted;
$A^{69}$ is Ser, D-Ser, Aib, Ala, Thr, or deleted;
$A^{70}$ is Ala, D-Ala, Asn, Asp, Gln, Glu, or deleted;
$A^{71}$ is Asn, Ala, Asp, Gln, Glu, Lys, Ser, Thr, or deleted; and
$R^1$ is OH or $NH_2$;
provided that the side-chains of residue pairs $A^6$ and $A^{48}$, $A^{47}$ and $A^{52}$, and $A^{18}$ and $A^{61}$, each form a disulfide bond; and
further provided that when $A^{59}$ is either Leu, Ile, Nle, Thr, or Val, then the analogue contains at least one additional amino acid substitution or addition as defined herein.

In the formula (I), preferred amino acid substitutions and additions are defined as follows:
$A^{-1}$ is Met, Ser or deleted;
$A^1$ is Gly or deleted;
$A^2$ is Pro, Lys, or deleted;
$A^3$ is Glu or deleted;
$A^4$ is Thr;
$A^5$ is Leu;
$A^6$ is Cys, hCys, β-Me-Cys, N-Me-Cys, or Pen;
$A^7$ is Gly;
$A^8$ is Ala;

$A^9$ is Glu;
$A^{10}$ is Leu;
$A^{11}$ is Val;
$A^{12}$ is Asp;
$A^{13}$ is Ala;
$A^{14}$ is Leu;
$A^{15}$ is Gln;
$A^{16}$ is Phe;
$A^{17}$ is Val;
$A^{18}$ is Cys, hCys, β-Me-Cys, N-Me-Cys, or Pen;
$A^{19}$ is Gly;
$A^{20}$ is Asp;
$A^{21}$ is Arg;
$A^{22}$ is Gly;
$A^{23}$ is Phe;
$A^{24}$ is Tyr;
$A^{25}$ is Phe;
$A^{26}$ is Asn;
$A^{27}$ is Lys, Arg, or Pro;
$A^{28}$ is Pro or Lys;
$A^{29}$ is Thr;
$A^{30}$ is Gly;
$A^{31}$ is Tyr;
$A^{32}$ is Gly;
$A^{33}$ is Ser;
$A^{34}$ is Ser;
$A^{35}$ is Ser;
$A^{36}$ is Arg;
$A^{37}$ is Arg;
$A^{38}$ is Ala;
$A^{39}$ is Pro;
$A^{40}$ is Gln;
$A^{41}$ is Thr;
$A^{42}$ is Gly;
$A^{43}$ is Ile;
$A^{44}$ is Val;
$A^{45}$ is Asp;
$A^{46}$ is Glu;
$A^{47}$ is Cys, hCys, β-Me-Cys, N-Me-Cys, or Pen;
$A^{48}$ is Cys, hCys, β-Me-Cys, N-Me-Cys, or Pen;
$A^{49}$ is Phe, Arg, Leu, or Thr;
$A^{50}$ is Arg or Ser;
$A^{51}$ is Ser, Aib, Arg, or Thr;
$A^{52}$ is Cys, hCys, β-Me-Cys, N-Me-Cys, or Pen;
$A^{53}$ is Asp, Arg, or Ser;
$A^{54}$ is Leu or A6c;
$A^{55}$ is Arg or Tyr;
$A^{56}$ is Arg or Gln;
$A^{57}$ is Leu;
$A^{58}$ is Glu or Arg;
$A^{59}$ is A6c, Arg, Asn, Asp, Gln, Glu, Ile, Leu, Nle, Ser, D-Ser, Trp, or Tyr;
$A^{60}$ is Tyr or Phe;
$A^{61}$ is Cys, hCys, β-Me-Cys, N-Me-Cys, or Pen;
$A^{62}$ is Ala or Asn;
$A^{63}$ is Pro, D-Pro, Thr, or deleted;
$A^{64}$ is Leu, D-Leu, des-Leu, or deleted;
$A^{65}$ is Lys, D-Lys, des-Lys, Arg, or deleted;
$A^{66}$ is Pro, D-Pro, or deleted;
$A^{67}$ is Ala, D-Ala, Aib, or deleted;
$A^{68}$ is Lys, D-Lys, Arg, or deleted;
$A^{69}$ is Ser, D-Ser, Aib, Thr, or deleted;
$A^{70}$ is Ala, D-Ala, Glu, or deleted; and
$A^{71}$ is Asp, Glu, Lys, Ser, or deleted.

A subset of the compounds covered by the formula (I) encompasses compounds in which $A^{59}$ is Asn.

Another subset of the compounds covered by the formula (I) encompasses compounds in which $A^{59}$ is Leu, wherein said compounds contain at least one additional amino acid substitution or addition selected from the group consisting of $Arg^{27}$, $Are^{65}$, $Arg^{68}$, $Leu^{49}$, $β-Me-Cys^{47}$, $β-Me-Cys^{52}$, $Thr^{51}$, $Thr^{69}$, $Asp^{71}$, $Glu^{71}$, $Lys^{71}$, and $Ser^{71}$.

Yet another subset of the compounds covered by the formula (I) encompasses compounds in which $A^{59}$ is Nle, wherein said compounds contain at least one additional amino acid substitution selected from the group consisting of $Aib^{51}$, $Aib^{67}$, $Aib^{69}$, $A6c^{54}$, $N-Me-Cys^{47}$, $N-Me-Cys^{48}Pen^{52}$, and $Pen^{61}$.

Yet another subset of the compounds covered by the formula (I) encompasses compounds in which $A^{59}$ is Ile, wherein said compounds contain at least one more amino acid substitution selected from the group consisting of $Are^{58}$, $Arg^{49}$, $Arg^{51}$, and $Arg^{53}$.

Yet another subset of the compounds covered by the formula (I) encompasses compounds in which $A^{59}$ is Arg, Asp, A6c, Gln, Glu, Ser, Trp, or Tyr.

Preferred compounds of the formula (I) are:
Example 1: $(Asn^{59})$hIGF-1(1-70)-OH; (SEQ ID NO:1)
Example 2: $(Asn^{59})$hIGF-1(1-62)-OH; (SEQ ID NO:2)
Example 3: $(Asn^{59})$hIGF-1(4-70)-OH; (SEQ ID NO:3)
Example 4: $(Pro^{27}, Lys^{28}, Asn^{59})$hIGF-1(1-70)-OH; (SEQ ID NO:4)
Example 5: $(Pro^{27}, Lys^{28}, Asn^{59})$hIGF-1(1-62)-OH; (SEQ ID NO:5)
Example 6: $(Ser^{53}, Asn^{59})$hIGF-1(1-70)-OH; (SEQ ID NO:6)
Example 7: $(Ser-Gly^1, Asn^{59})$hIGF-1(1-70)-OH; (SEQ ID NO:7)
Example 8: $(Asn^{59}, Thr^{63}, des-Leu^{64}, des-Lys^{65}, Glu^{70})$hIGF-1(1-70)-OH; (SEQ ID NO:8)
Example 9: $(Tyr^{55}, Asn^{59})$hIGF-1(1-70)-OH; (SEQ ID NO:9)
Example 10: $(Thr^{49}, Asn^{59})$hIGF-1(1-70)-OH; (SEQ ID NO:10)
Example 11: $(Asn^{59,62})$hIGF-1(1-70)-OH; (SEQ ID NO:11)
Example 12: $(Asn^{59}, Phe^{60})$hIGF-1(1-70)-OH; (SEQ ID NO:12)
Example 13: $(Ser^{50}, Asn^{59})$hIGF-1(1-70)-OH; (SEQ ID NO:13)
Example 14: $(Gln^{56}, Asn^{59})$hIGF-1(1-70)-OH; (SEQ ID NO:14)
Example 15: $(Asn^{59}, D-Pro^{63})$hIGF-1(1-70)-OH;
Example 16: $(Asn^{59}, D-Leu^{64})$hIGF-1(1-70)-OH;
Example 17: $(Asn^{59}, D-Lys^{65})$hIGF-1(1-70)-OH;
Example 18: $(Asn^{59}, D-Pro^{66})$hIGF-1(1-70)-OH;
Example 19: $(Asn^{59}, D-Ala^{69})$hIGF-1(1-70)-OH;
Example 20: $(Asn^{59}, D-Lys^{68})$hIGF-1(1-70)-OH;
Example 21: $(Asn^{59}, D-Ser^{69})$hIGF-1(1-70)-OH;
Example 22: $(Asn^{59}, D-Ala^{70})$hIGF-1(1-70)-OH;
Example 23: $(Arg^{27,65,68}, Leu^{59})$hIGF-1(1-70)-OH; (SEQ ID NO:15)
Example 24: $(Leu^{59}, Arg^{65,68})$hIGF-1(1-70)-OH; (SEQ ID NO:16)
Example 25: $(Leu^{49,59})$hIGF-1(1-70)-OH; (SEQ ID NO:17)
Example 26: $(β-Me-Cys^{52}, Leu^{59})$hIGF-1(1-70)-OH; (SEQ ID NO:18)
Example 27: $(β-Me-Cys^{47}, Leu^{59})$hIGF-1(1-70)-OH; (SEQ ID NO:19)
Example 28: $(Leu^{59}, Glu^{71})$hIGF-1(1-71)-OH; (SEQ ID NO:20)
Example 29: $(Leu^{59}, Asp^{71})$hIGF-1(1-71)-OH; (SEQ ID NO:21)
Example 30: $(Leu^{59}, Lys^{71})$hIGF-1(1-71)-OH; (SEQ ID NO:22)

Example 31: (Leu⁵⁹, Ser⁷¹)hIGF-1(1-71)-OH; (SEQ ID NO:23)
Example 32: (Leu⁵⁹, Thr⁶⁹)hIGF-1(1-70)-OH; (SEQ ID NO:24)
Example 33: (Thr⁵¹, Leu⁵⁹)hIGF-1(1-70)-OH; (SEQ ID NO:25)
Example 34: (N-Me-Cys⁴⁷, Nle⁵⁹)hIGF-1(1-70)-OH; (SEQ ID NO:26)
Example 35: (Nle⁵⁹, Aib⁶⁹)hIGF-1(1-70)-OH; (SEQ ID NO:27)
Example 36: (N-Me-Cys⁴⁸, Nle⁵⁹)hIGF-1(1-70)-OH; (SEQ ID NO:28)
Example 37: (Nle⁵⁹, Aib⁶⁷)hIGF-1(1-70)-OH; (SEQ ID NO:29)
Example 38: (hCys⁵², Nle⁵⁹)hIGF-1(1-70)-OH; (SEQ ID NO:30)
Example 39: (Aib⁵¹, Nle⁵⁹)hIGF-1(1-70)-OH; (SEQ ID NO:31)
Example 40: (Pen⁵², Nle⁵⁹)hIGF-1(1-70)-OH; (SEQ ID NO:32)
Example 41: (Nle⁵⁹, Pen⁶¹)hIGF-1(1-70)-OH; (SEQ ID NO:33)
Example 42: (A6c⁵⁴, Nle⁵⁹)hIGF-1(1-70)-OH; (SEQ ID NO:34)
Example 43: (Arg⁵³, Ile⁵⁹)hIGF-1(1-70)-OH; (SEQ ID NO:35)
Example 44: (Arg⁴⁹, Ile⁵⁹)hIGF-1(1-70)-OH; (SEQ ID NO:36)
Example 45: (Arg⁵¹, Ile⁵⁹)hIGF-1(1-70)-OH; (SEQ ID NO:37)
Example 46: (Arg⁵⁸, Ile⁵⁹)hIGF-1(1-70)-OH; (SEQ ID NO:38)
Example 47: (A6c⁵⁹)hIGF-1(1-70)-OH; (SEQ ID NO:39)
Example 48: (Asp⁵⁹)hIGF-1(1-70)-OH; (SEQ ID NO:40)
Example 49: (Trp⁵⁹)hIGF-1(1-70)-OH; (SEQ ID NO:41)
Example 50: (Ser⁵⁹)hIGF-1(1-70)-OH; (SEQ ID NO:42)
Example 51: (Tyr⁵⁹)hIGF-1(1-70)-OH; (SEQ ID NO:43)
Example 52: (Glu⁵⁹)hIGF-1(1-70)-OH; (SEQ ID NO:44)
Example 53: (Gln⁵⁹)hIGF-1(1-70)-OH; (SEQ ID NO:45)
Example 54: (Arg⁵⁹)hIGF-1(1-70)-OH; and (SEQ ID NO:46)
Example 55: (Met-Gly¹, Asn⁵⁹)hIGF-1(1-70)-OH. (SEQ ID NO:47)

DETAILED DESCRIPTION OF THE INVENTION

The application employs the following commonly understood abbreviations:
Acc: 1-amino-1-cyclo(C₃-C₉)allyl carboxylic acid
  Acc includes:
    A3c: 1-amino-1-cyclopropanecarboxylic acid
    A4c: 1-amino-1-cyclobutanecarboxylic acid
    A5c: 1-amino-1-cyclopentanecarboxylic acid
    A6c: 1-amino-1-cyclohexanecarboxylic acid
Aib: α-aminoisobutyric acid
Ala or A: alanine
Arg or R: arginine
Asn or N: asparagine
Asp or D: aspartic acid
Cys or C: cysteine
cystine: disulfide dimer of cysteine
hCys: homocysteine β-Me-Cys: beta-methyl-cysteine, i.e., (2S,3S)-2-amino-3-mercaptobutyric acid
N-Me-Cys: N-methyl-cysteine
Gln or Q: glutamine
Glu or E: glutamic acid
Gly or G: glycine
Ile or I: isoleucine
Leu or L: leucine
des-Leu: deleted Leu
Lys or K: lysine
des-Lys: deleted Lys
Met or M: methionine
Nle: norleucine
Pen: penicillamine
Phe or F: phenylalanine
Pro or P: proline
Ser or S: serine
Thr or T: threonine
Trp or W: tryptophan
Tyr or Y: tyrosine
Val or V: valine All abbreviations (e.g., Ala) of amino acids in this disclosure stand for the structure of —NR—CR'(R")—CO—, wherein R' and R" each is, independently, hydrogen or the side chain of an amino acid (e.g., R'=H and R"=CH₃ for alanine) and wherein R=H or CH₃, except for proline,

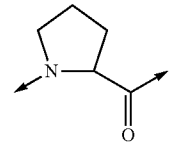

i.e.,

A peptide of this invention is also denoted herein by another format, e.g., (Asn⁵⁹)hIGF-1(1-70)-OH (SEQ ID NO:1), with the substituted amino acids from the natural sequence placed between the parentheses (i.e., Asn for Met at position 59 of the wild-type IGF-1). The range found within the parentheses refers to those amino acids found in the analogue. For example, "IGF-1(4-68)-OH" (SEQ ID NO:48) indicates that the analogue is comprised of amino acids 4 through 68 which correspond to the peptide sequence for the wild-type IGF-1. "NH₂" in "IGF-1(1-70)-NH₂" (SEQ ID NO:49) indicates that the C-terminus of the peptide is amidated. "IGF-1(1-70)" or "IGF-1(1-70)-OH" indicates that the C-terminus is the free acid (SEQ ID NO:50).

Certain other abbreviations used herein are defined as follows:
Act: acetonitrile
Boc: Cert-butyloxycarbonyl
BSA: bovine serum albumin
DCM: dichloromethane
DIPEA: diisopropylethylamine
DMEM: Dulbecco's Modified Eagle's Medium
DMF: dimethylformamide
DTT: dithiothrieitol
ESI: electrospray ionization
FCS: fetal calf serum
Fmoc: 9-fluorenylmethyloxycarbonyl
HBTU: 2-(1H-benzotriazole-1-yl)-1,1,3,3-tetramethyluronium hexafluorophosphate
HOBt: N-hydroxybenzotriazole
HPLC: high performance liquid chromatography
LC-MS: liquid chromatography mass spectrometry
MPAA: 4-mercaptophenylacetic acid
NMP: N-methylpyrrolidinone
OtBu: O-tert-butyl ester
Pbf: 2,2,4,6,7-pentamethyldihydrobenzofuran-5-sulfonyl
QC: quality control
tBu: tert-butyl
TCA: trichloroacetic acid
TCEP tris-2-carboxyethyl-phosphine TIS: triisopropylsilane
TFA: trifluoroacetic acid
Tris: 2-amino-2-(hydroxymethyl)-1,3-propanediol
Trt: trityl
UV spectroscopy: ultraviolet spectroscopy "Alkyl" refers to a hydrocarbon group containing one or more carbon atoms wherein multiple carbon atoms, if present, are joined by single bonds. Examples of which include, but are not limited to, methyl, ethyl, propyl, and butyl. The alkyl hydrocarbon group may be straight-chain or contain one or more branches or cyclic groups, examples of which include, but are not limited to, isopropyl and tert-butyl.

"Substituted alkyl" refers to an alkyl wherein one or more hydrogen atoms of the hydrocarbon group are replaced with one or more substituents selected from the group consisting of halogen, OH, CN, SH, $NH_2$, $NHCH_3$, $NO_2$, ($C_{1-2}$) alkyl substituted with 1 to 6 halogens, $CF_3$, $OCH_3$, $OCF_3$, and $(CH_2)_{0-4}$—COOH. In different embodiments, 1, 2, 3 or 4 substituents are present.

"Aryl" refers to an optionally substituted aromatic group with at least one ring having a conjugated pi-electron system, containing up to three conjugated or fused ring systems. Aryl includes carbocyclic aryl, heterocyclic aryl and biaryl groups. Preferably, the aryl is a 5 or 6 membered ring. Preferred atoms for a heterocyclic aryl are one or more sulfur, oxygen, and/or nitrogen. Examples of aryl include phenyl, 1-naphthyl, 2-naphthyl, indole, quinoline, 2-imidazole, and 9-anthracene. Aryl substituents are selected from the group consisting of —$C_{1-20}$ alkyl, —$C_{1-20}$ alkoxy, halogen, —OH, —CN, —SH, —$NH_2$, —$NO_2$, —$C_{1-20}$ alkyl substituted with halogens, —$CF_3$, —$OCF_3$, and —$(CH_{0-20}$—COOH. In different embodiments the aryl contains 0, 1, 2, 3, or 4 substituents.

"Alkyl-aryl" refers to an "alkyl" joined to an "aryl".

Synthetic Procedures

The exemplified analogues of IGF-1 of the present invention were prepared by a first step of peptide fragment synthesis, a second step of ligation, and a third step of folding. The following synthetic procedures illustrate how a skilled chemist would be enabled to prepare any one of the exemplified analogues of IGF-1 of the present invention.

A) Peptide fragment synthesis of ($Gln^{56}$, $Asn^{59}$)hIGF-1 (48-70)-OH, i.e., Cys-Phe-Arg-Ser-Cys-Asp-Leu-Arg-Gln-Leu-Glu-Asn-Tyr-Cys-Ala-Pro-Leu-Lys-Pro-Ala-Lys-Ser-Ala-OH (SEQ ID NO:51)

Fmoc-based solid-phase peptide synthesis was used to assemble the titled peptide fragment using microwave assistance on a Liberty Peptide Synthesizer (CEM; Matthews, N.C., USA). The first 14-residue fragment, i.e., residues 57-70 of hIGF-1, or the C-terminal acid peptide, was synthesized on a 1.0-mmole scale using Fmoc-Ala-Wang resin (0.72 meq/g). The resulting peptide fragment was then split into four 0.25-mmole batches for elongation and differentiation. A 1.36 g resin sample was placed in a 50-mL conical tube together with 15 mL of a 1:1 solution of DMF and DCM which was loaded into position in the synthesizer. The resin was then transferred to the reaction vessel via the synthesizer's automated process. The standard Liberty protocol for 1.0-mmole scale synthesis was used. The protocol involved removal of the N-terminal Fmoc protecting group by treatment with 20 mL of 20% piperidine containing 0.1M HOBt in DMF. The initial de-protection step of microwave power (45 watts, maximum temperature of 75° C.) and nitrogen bubbling (3 seconds on, 7 seconds off) lasted for 30 seconds. The reaction vessel was drained and the resin was washed thoroughly with DMF several times. The next amino acid (Cycle 1) to be added to the growing peptide, (Fmoc-Ser(tBu)-OH) prepared as a 0.2M stock solution in DMF, was then added (15 mL, 3 equivalents). 6.0 mL of 0.45M (3 equivalents) HBTU in DMF was added followed by 3.0 mL of 2M (6 equivalents) DIPEA in NMP. The coupling step was performed using microwave power (20 watts, maximum temperature of 75° C.) with nitrogen bubbling at the same rate as in the de-protection step for a period of 5 minutes. The reaction vessel was then drained to waste and the coupling step was repeated.

The coupling protocol for Fmoc-Cys(Trt)-OH was a slightly modified version of the standard protocol. For Cys residues, no microwave power was applied for the first 2 minutes. A 4-minute session of microwave power (20 watts, maximum temperature of 50° C.) followed. All amino acids were introduced similarly, employing a double coupling strategy throughout the entire sequence. The synthesis cycles for the titled peptide fragment following the first Ser were as follows: Cycle 2, Fmoc-Lys(Boc)-OH; Cycle 3, Fmoc-Ala-OH; Cycle 4, Fmoc-Pro-OH; Cycle 5, Fmoc-Lys(Boc)-OH; Cycle 6, Fmoc-Leu-OH; Cycle 7, Fmoc-Pro-OH; Cycle 8, Fmoc-Ala-OH; Cycle 9, Fmoc-Cys(Trt)-OH; Cycle 10, Fmoc-Tyr(tBu)-OH; Cycle 11, Fmoc-Asn(Trt)-OH; Cycle 12, Fmoc-Glu(OtBu)-OH; and Cycle 13, Fmoc-Leu-OH.

Once the initial peptide fragment was completed, the resin was transferred back to the 50-mL conical tube using DMF as a solvent. The resin was manually split evenly into four samples which were put into four 50-mL conical tubes which were then put back into the synthesizer. The remaining portion of the titled peptide was synthesized on a 0.25-mmole scale. The protocol used was the same as that used for the larger scale synthesis, however, lesser amounts of reagents were used. Removal of the N-terminal Fmoc protecting group consisted of treatment with a solution containing 10 mL of 20% piperidine and 0.1M HOBt in DMF. The initial de-protection step of microwave power (45 watts, maximum temperature of 75° C.) with nitrogen bubbling (3 seconds on, 7 seconds off) lasted for 30 seconds. The reaction vessel was then drained and the resin was washed several times thoroughly with DMF. The next amino acid (Cycle 14), prepared as a 0.2M stock solution in DMF, was then introduced (5.0 mL, 4 equivalents) to the growing peptide (Fmoc-Gln(tBu)-OH). 2.0 mL of a 0.45M solution (4 equivalents) of HBTU in DMF was then added followed by 1.0 mL of a 2M solution (8 equivalents) of DIPEA in NMP.

The coupling protocols for Fmoc-Cys(Trt)-OH and Fmoc-Arg(Pbf)-OH were slightly modified versions of the standard protocol. For the coupling of Cys residues, the microwave power was initially off for the first 2 minutes then turned on for 4 minutes (20 watts, maximum temperature of 50° C.). For the coupling of Arg residues, microwave power was not employed in the first coupling, however, a second standard coupling step was required. Cycles 14, 16 and 21 employed a capping procedure which immediately followed the coupling step, which involved adding 7 mL of 0.5M acetic anhydride containing 0.015M HOBt and 2 mL of 2M DIPEA both in NMP while utilizing a multi-step microwave protocol (50 watts for 30 seconds with a maximum temperature of 65° C., then no power for 30 seconds, 50 watts for 30 seconds with a maximum temperature of 65° C., then no power for 30 seconds). The synthesis cycles for the titled peptide fragment after Gln were as follows: Cycle15, Fmoc-Arg(Pbf)-OH; Cycle 16, Leu-OH; Cycle 17, Fmoc-Asp(OtBu)-OH; Cycle 18, Fmoc-Cys(Trt)-OH; Cycle 19, Fmoc-Ser(tBu)-OH; Cycle 20, Fmoc-Arg(Pbf)-OH; Cycle 21, Fmoc-Phe-OH; and Cycle 22, Fmoc-Cys(Trt)-OH.

Following completion of the peptide backbone, the N-terminal Fmoc-protecting group was removed and the resin was washed again with DMF. The resin was then transferred back to the 50-mL conical tube using DMF as the transfer solvent.

The resin was transferred into a reaction vessel with a sintered glass frit. The DMF was removed and the resin was washed extensively with DCM. The peptide fragment was cleaved and de-protected by treatment with the following reagent: 5% TIS: 5% water: 90% TFA. The reaction was allowed to proceed for 3 hours at room temperature with constant shaking. The solution was then filtered into a 50-mL conical tube. TFA was reduced by evaporation with nitrogen gas flow. The peptide fragment was precipitated by the addition of 40 mL of cold ethyl ether followed by centrifugation at 3000 rpm for 30 minutes at 4° C. within a refrigerated centrifuge (Sorvall Legend RT; Thermo Fisher, San Jose, Calif., USA). The resulting pellet was dissolved in 0.1% TFA water before purification by preparative HPCL equipped with a C18 reverse phase column (Luna, 10 µm, 250×21.2 mm column) utilizing a gradient of 0-60% acetonitrile (0.1% TFA) over 50 minutes with a flow rate of 10 mL/min. The purified peptide fragment was analyzed by HPLC (Luna C18, 3 µm, 4.6×100 mm column) with a gradient of 5-80% acetonitrile (0.08% TFA) over 30 minutes with a flow rate of 1 mL/min and by mass spectrometry (LCQ Advantage; Thermo Fisher, San Jose, Calif., USA). The peptide fragment was subsequently lyophilized and stored at −50° C. for future use.

B) Peptide Fragment Synthesis of hIGF-1(1-47)-thioester. i.e., Gly-Pro-Glu-Thr-Leu-Cys-Gly-Ala-Glu-Leu-Val-Asp-Ala-Leu-Gln-Phe-Val-Cys-Gly-Asp-Arg-Gly-Phe-Tyr-Phe-Asn-Lys-Pro-Thr-Gly-Tyr-Gly-Ser-Ser-Ser-Arg-Arg-Ala-Pro-Gln-Thr-Gly-Ile-Val-Asp-Glu-Cys-thioester-propionyl-Leu-NH$_2$ (SEQ ID NO:52)

The N-terminal peptide fragment, i.e., residues 1-47 of hIGF-1, was assembled using Boc-chemistry based solid-phase peptide synthesis. An ABI 433A peptide synthesizer (Applied Biosystems; Foster City, Calif., USA) modified to run the standard FastBoc protocol was utilized for the 0.5-mmole scale synthesis. The reaction vessel containing 0.645 mg of 0.77 meq/g of Tampal Resin was placed on the synthesizer. To swell the resin, DMF was introduced. The ABI FastBoc 0.5 protocol was used to generate the fragment. Each cycle consisted of de-blocking the N-terminal Boc protecting group with neat TFA followed by extensive DMF washing. Pre-packaged 2.0-mmole (4 equivalents) cartridges of each amino acid were then dissolved in 0.40M HBTU and DMF. After complete dissolution of each amino acid, the solution was automatically transferred to the activation vessel. A DIPEA solution (neat) was introduced to the activation vessel and was exposed to the resin for an extended period. The reaction vessel was emptied and the resin was washed with DMF. For Arg/Asn cartridges, an extended activation time was required to ensure solubility. In addition, any amino acid added immediately after the coupling of a Gln residue was washed with DCM both before and after the deblocking protocol. The coupling times were 30 minutes. The following amino acids were used for the titled peptide fragment: Boc-Arg(Tos)-OH, Boc-Asp(cHex)-OH, Boc-Glu(cHex)-OH, Boc-Asn(Xan)-OH, Boc-Cys(4Me-Bzl)-OH, Boc-Lys(ClZ)-OH, Boc-Gln-OH, Boc-Ser(OBzl)-OH, Boc-Thr(OBzl)-OH, and Boc-Tyr(BrZ)-OH.

Following the last coupling cycle, the resin was washed with DCM and dried. The peptide fragment was de-protected and cleaved from the resin using a treatment with 10 mL of hydrogen fluoride and anisole. The reaction was allowed to proceed for 70 minutes at which point the hydrogen fluoride was blown off with a stream of nitrogen. The residue was washed with ether and then the peptide was dissolved in 10-15 ml of TFA. The peptide fragment was precipitated by filtering the TFA into 40 mL of cold ethyl ether followed by centrifugation at 3000 rpm for 30 minutes at 4° C. within a refrigerated centrifuge (Sorvall Legend RT; Thermo Fisher, San Jose, Calif., USA). The resulting pellet was dissolved in 0.1% TFA water and was purified by preparative HPLC equipped with a C18 reverse phase column (Luna, 10 µm, 250×21.2 mm column) utilizing a gradient of 20-40% acetonitrile (0.1% TFA) over 120 minutes with a flow rate of 10 mL/min. The purified peptide fragment was analyzed by HPLC (Luna C18, 3 µm, 4.6×100 mm column) with a gradient of 5-80% acetonitrile (0.08% TFA) for 30 minutes with a flow rate of 1 mL/min and by mass spectrometry (LCQ Advantage; Thermo Fisher, San Jose, Calif., USA). The peptide fragment was subsequently lyophilized and stored at −50° C. for future use.

C) General Ligation Procedure

Full length hIGF-1 analogues were constructed the chemical ligation method that naturally occurs between an N-terminal thioester fragment, e.g., hIGF-1(1-47)-S—(CH$_2$)$_2$C(O)-Leu-NH$_2$ (SEQ ID NO:52), and a C-terminal fragment, e.g., (Gln$^{56}$, Asn$^{59}$)hIGF-1(48-70)-OH (SEQ ID NO:51), which contains a cysteine residue at its N-terminus.

To commence the process for the titled peptide, 5.5 mg of the C-terminal hIGF-1 fragment was dissolved in 0.5 mL of ligation buffer (200 mM sodium phosphate, pH 8.5, 6M guanidine hydrochloride) in a 1.5-mL eppendorf tube. To this solution, 100 µL of a TCEP solution (40 mg/mL) was added and the mixture was vortexed. The mixture was transferred to a second eppendorf tube containing 6.5 mg of the N-terminal hIGF-1 thioester fragment. The reactants were mixed thoroughly. A small sample (5 µL) was removed and analyzed by LC-MS (LCQ Deca XP; Thermo Fisher, San Jose, Calif., USA). To the reaction mixture, 100 µL of a MPAA solution (20 mg/mL) was added followed by mixing. Samples (5 µL) were periodically extracted in order to follow the progress of the reaction using LC-MS. After approximately 3.5 hours when the reaction was near completion, the mixture was quenched and diluted by the addition of 9.5 mL of 0.1% TFA water. The ligation product was purified by SemiPrep-HPLC (Vydac 218TP101510, C18, 10-15 µm, 10×250 mm) with a gradient of 5-80% acetonitrile (0.1% TFA) over 40 minutes with a flow rate of 5 mL/min. The product peak was lyophilized and stored at −50° C. The mass of the unfolded ligation product was determined by physical measurement.

D) General Folding Procedure (Glutathione Redox Pair) for Example 14, i.e. (Gln$^{56}$, Asn$^{59}$)hIGF-1(1-70)-OH (SEQ ID NO:14)

The protein, prepared by the ligation process of step C) as described above, was dissolved in ligation buffer (200 mM sodium phosphate, pH 8.5, 6M guanidine hydrochloride) to a concentration of 1 mg/mL. Folding buffer (100 mM Tris, pH 8.5, 1 mM oxidized glutathione, 10 mM reduced glutathione) was then added to bring the final protein concentration to 0.25 mg/mL. The folding process was allowed to occur over 3 hours. Afterwards, the reaction was quenched by the dropwise addition of TFA until the reaction mixture reached pH≤3. The product was then purified by SemiPrep-HPLC (Vydac 218TP101510, C18, 10-15 µm, 10×250 mm column) with a gradient of 5-60% acetonitrile (0.1% TFA) over 40 minutes with a flow rate of 5 mL/min. The product was lyophilized. The protein content was determined by re-dissolving the product in 0.1% TFA water then measuring the absorbance at 280 nm (NanoDrop ND 1000 Spectrophotometer). The protein was then analyzed for QC (HPLC and MS).

E) Oxidation Procedure for the Formation of (Glyoxylyl-Gly$^1$, Asn$^{59}$)hIGF-1 (1-70)-OH (SEQ ID NO:53) from Example 7, i.e. (Ser-Gly$^1$, Asn$^{59}$)hIGF-1(1-70)-OH (SEQ ID NO:7)

The mass of the folded hIGF-1 analogue was determined by absorbance at 280 nm in 0.1% TFA water (NanoDrop ND1000 Spectrophotometer). The protein, prepared by the folding process of step D) as described above, was re-dissolved in 50 mM imidazole buffer (pH 7.0) to a final concentration of 2 mg/mL ($2.66 \times 10^{-4}$M). Sodium periodinate (NaIO$_4$) (4 equivalents) dissolved in an imidazole buffer was added and the resulting solution was gently mixed. The reaction was allowed to proceed at room temperature without further agitation. After 5 minutes, the reaction was quenched with the addition of 10 equivalents of ethylene glycol. The mixture was allowed to stand for 15 minutes at room temperature. The mixture was diluted with 0.1% TFA water to a final volume of 10 mL. The product was then purified by SemiPrep-HPLC (Vydac 218TP101510, C18, 10-15 μm, 10×250 mm column) with a gradient of 5-60% acetonitrile (0.1% TFA) for 40 minutes with a flow rate of 5 mL/min. The product was then lyophilized and stored at −50° C. until needed.

F) Synthetic Procedure for Example 27, i.e., (β-Me-Cys$^{47}$, Leu$^{59}$)hIGF-1(1-70)-OH (SEQ ID NO:19)

The titled protein was assembled through native chemical ligation using hIGF(1-46)-thio-propionyl-Leu-NH$_2$ (SEQ ID NO:54) and the C-terminal fragment, i.e., (β-Me-Cys$^{47}$, Leu$^{59}$)hIGF-1(47-70) (SEQ ID NO:55). The protein thioester (7.4 mg, 1.45 gmoles) and the C-terminal fragment (3.8 mg, 1.38 gmoles) were dissolved in ligation buffer (6M guanidine hydrochloride in 200 mM sodium phosphate, pH 8.5, 400 μL) and TCEP (80 μL, 40 mg/mL, pH 7). An MPAA catalyst was added (80 μL, 20 mg/mL, pH 7). The reaction progress was monitored on a LCQ Deca XP LC-MS (Thermo Finnigan) with a Luna C18(2) column (5 μm, 4.6×100 mm) with a gradient of 5-80% acetonitrile (0.1% TFA) for 30 minutes. The reaction was quenched to a dilution of 1:10 with dH$_2$O, 0.1% TFA (v/v). The crude mixture was centrifuged and passed through a 1.0-μm glass filter to remove any MPAA precipitate. The full length protein was purified using a 5-60% B linear gradient for 40 minutes with a flow rate of 5 mL/min on a Vydac C18 (10 μm, 10×250 mm). The protein was quantitated by UV spectroscopy (NanoDrop ND1000 Spectrophotometer) and lyophilized for future use.

The stored protein (1.8 mg, 235 nmoles) was dissolved in a 200 mM H$_2$PO$_4^-$, 6M guanidinium-HCl solution having pH 8.5 to a concentration of 1.0 mg/mL. Folding buffer (100 mM Tris, 10 mM glutathione, 1 mM oxidized glutathione at pH 8.5) was added to the solution until a final protein concentration of 250 μg/mL was achieved. The mixture was allowed to incubate at room temperature while being monitored by HPLC. Once equilibrium was reached (as visualized by a stable HPLC profile), the reaction was quenched by stirring in either acetic acid or TFA to bring the solution to pH 3. The solution purified using first a 1.0-μm glass filter and then a semi-preparative column.

The folded protein was purified using a 5-60% B linear gradient for 40 minutes with a flow rate of 5 mL/min. The protein was quantitated by UV (NanoDrop ND1000 Spectrophotometer) and lyophilized. Approximately 92 μg of purified product was obtained, representing a yield of 5%. The mass of the protein was verified on a Finnigan LCQ Advantage MAX MS.

G) Synthetic Procedure for Example 36, i.e. (N-Me-Cys$^{48}$, Nle$^{59}$)hIGF-1(1-70)-OH (SEQ ID NO:28)

The titled protein was assembled utilizing native chemical ligation using hIGF-1(1-47)-thio-propionyl-Leu-NH$_2$ (SEQ ID NO:52) and the C-terminal fragment, i.e., (N-Me-Cys$^{48}$, Nle$^{59}$)hIGF-1(48-70) (SEQ ID NO:56). The protein thioester (4.3 mg, 824 nmoles) and the C-terminal fragment (2.1 mg, 790 nmoles) were dissolved in ligation buffer (400 μL, 6M guanidine hydrochloride in 200 mM sodium phosphate, pH 8.5) and TCEP (80 μL, 40 mg/mL, pH 7). An MPAA catalyst was added (80 μL, 20 mg/mL, pH 7). The reaction progress was monitored using a Finnigan LCQ Deca XP LC-MS with a Luna C18(2) column (5 μm, 4.6×100 mm) having a gradient of 5-80% acetonitrile (0.1% TFA) for 30 minutes. The reaction was quenched to a dilution of 1:10 with dH$_2$O, 0.1% TFA (v/v). The crude mixture was centrifuged and passed through a 1.0 μm glass filter to remove any MPAA precipitate. The full length protein was purified using a Vydac C18 (10 μm, 10×250 mm) with a 5-60% B linear gradient for 40 minutes with a flow rate of 5 mL/min. The protein was quantitated by UV (NanoDrop ND1000 Spectrophotometer) and lyophilized for future use.

The stored protein was dissolved using a 200 mM H$_2$PO$_4^-$, 6M guanidinium-HCl solution (pH 8.5) until a concentration of 1.0 mg/mL was achieved. Folding buffer (100 mM Tris, 10 mM glutathione, 1 mM oxidized glutathione, pH 8.5) was added to the solution until a final protein concentration of 250 μg/mL was achieved. The mixture was allowed to incubate at room temperature while being monitored by HPLC. Once equilibrium was reached (as visualized by a stable HPLC profile), the reaction was quenched with either acetic acid or TFA to pH 3. The solution was purified using first a 1.0-μm glass filter and then a semi-preparative column.

The folded protein was purified using a 5-60% B linear gradient with a flow rate of 5 mL/min for 40 minutes. The protein was quantitated by UV (NanoDrop ND1000 Spectrophotometer) and lyophilized. Approximately 0.415 mg of purified product was obtained, representing a yield of 10.6%. The mass of the protein was verified on a Finnigan LCQ Advantage MAX MS.

Other peptides of the invention can be prepared by a person of ordinary skill in the art using synthetic procedures analogous to those disclosed in the foregoing examples. Physical data for the compounds exemplified herein are given in Table 1.

TABLE 1

| Example Number | Mol. Wt. (Expected) | Mol. Wt. (ESI-MS) | % Purity (HPLC) |
|---|---|---|---|
| 1 | 7631.6 | 7631.6 | 99.9 |
| 2 | 6838.6 | 6839.5 | 95.2 |
| 3 | 7348.3 | 7347.9 | 93.0 |
| 4 | 7631.6 | 7632.1 | 97.7 |
| 5 | 6838.6 | 6839.3 | 95.9 |
| 6 | 7603.6 | 7602.5 | 99.9 |
| 7 | 7718.7 | 7718.7 | 99.9 |
| 8 | 7452.3 | 7454.1 | 99.9 |
| 9 | 7638.6 | 7639.7 | 99.9 |
| 10 | 7585.5 | 7586.0 | 99.9 |
| 11 | 7674.6 | 7675.3 | 99.9 |
| 12 | 7615.6 | 7616.9 | 99.9 |
| 13 | 7562.5 | 7563.6 | 99.9 |
| 14 | 7603.6 | 7605.1 | 98.5 |
| 15 | 7631.6 | 7634.1 | 96.8 |
| 16 | 7631.6 | 7633.2 | 97.2 |
| 17 | 7631.6 | 7632.9 | 95.1 |
| 18 | 7631.6 | 7631.6 | 96.7 |
| 19 | 7631.6 | 7631.9 | 97.9 |

TABLE 1-continued

| Example Number | Mol. Wt. (Expected) | Mol. Wt. (ESI-MS) | % Purity (HPLC) |
|---|---|---|---|
| 20 | 7631.6 | 7631.8 | 98.5 |
| 21 | 7631.6 | 7631.7 | 97.6 |
| 22 | 7631.6 | 7631.8 | 98.1 |
| 23 | 7714.7 | 7713.9 | 99.9 |
| 24 | 7686.7 | 7686.7 | 99.9 |
| 25 | 7596.6 | 7596.7 | 99.9 |
| 26 | 7644.7 | 7645.5 | 99.9 |
| 27 | 7644.7 | 7644.9 | 99.9 |
| 28 | 7759.8 | 7760.4 | 100 |
| 29 | 7745.8 | 7746.5 | 100 |
| 30 | 7758.8 | 7758.4 | 100 |
| 31 | 7717.7 | 7718.5 | 100 |
| 32 | 7644.7 | 7645.5 | 100 |
| 33 | 7644.7 | 7645.4 | 95.5 |
| 34 | 7644.7 | 7643.9 | 100 |
| 35 | 7628.7 | 7628.1 | 94.0 |
| 36 | 7644.7 | 7644.8 | 99.9 |
| 37 | 7644.7 | 7644.6 | 99.9 |
| 38 | 7644.7 | 7645.3 | 99.9 |
| 39 | 7628.7 | 7628.4 | 99.9 |
| 40 | 7658.7 | 7658.8 | 99.9 |
| 41 | 7658.7 | 7658.8 | 99.9 |
| 42 | 7642.7 | 7641.7 | 99.9 |
| 43 | 7671.8 | 7672.4 | 99.9 |
| 44 | 7641.7 | 7641.8 | 99.9 |
| 45 | 7699.8 | 7701.0 | 97.7 |
| 46 | 7657.7 | 7658.7 | 96.1 |
| 47 | 7642.7 | 7640.9 | 99.9 |
| 48 | 7632.6 | 7632.5 | 99.9 |
| 49 | 7703.7 | 7704.0 | 99.9 |
| 50 | 7604.6 | 7604.7 | 99.9 |
| 51 | 7680.7 | 7680.5 | 100 |
| 52 | 7646.6 | 7646.2 | 100 |
| 53 | 7645.6 | 7644.9 | 100 |
| 54 | 7673.7 | 7674.7 | 99.9 |

Functional Assays

A) In Vitro IGF-1 Receptor Binding Assay

Membranes were prepared for radioligand binding studies by homogenization of human MCF-7 cells expressing the native IGF-1 receptor in 20 ml of ice-cold 50 mM Tris-HCl with a Brinkman Polytron (Westbury, N.Y., USA) (setting 6, 15 sec). The homogenates were washed twice by centrifugation (39,000 g/10 minutes) and the final pellets were resuspended in 50 mM Tris-HCl containing 2.5 mM $MgCl_2$ and 0.1% BSA.

For the assay, aliquots were incubated with 0.05 nM [$^{125}$I] IGF-1. Unlabeled competing test peptides were sometimes included. The final assay volume was 0.25 ml. After a 120-minute incubation (20° C.) period, the bound [$^{125}$I]IGF-1 (~2000 Ci/mmol, Perkin Elmer Life Sciences, Boston, Mass., USA) was separated from the free radioactive particles by centrifugation at 3000 rpm for 10 minutes. The supernatant was decanted and the radioactive particles trapped in the pellet was counted by gamma spectrometry (Wallac LKB, Gaithersburg, Md., USA). Specific binding was defined as the total [$^{125}$I]IGF-1 bound minus that bound in the presence of 100 nM IGF-1.

In vitro IGF-1 receptor binding data (i.e. $IC_{50}$ values) for the compounds exemplified herein are given in Table 2.

B) In Vitro IGF-1 Bioactivity Assay

Mouse 3T3/R cells (obtained from Dr. E. Rozengurt at UCLA in Los Angeles, Calif., USA) were cultured on a 24-well plate (DMEM+10% FCS) and maintained for 2 days in culture.

For the assay, the media was removed and washed once with serum-free DMEM. The serum was then starved for 24 hours. After starvation, [$^3$H]thymidine and IGF-1 peptides were added. The cells were then incubated for 24 hours at 37° C.

At the end of the incubation, the media was aspirated. The cells were then washed with an ice-cold 0.9% NaCl solution. An ice-cold 5% TCA solution was then added for a 30-minute incubation at 4° C. The TCA was aspirated and the wells were incubated with 95% ethanol for 4 hours. The cell lysate was then transferred to a liquid scintillation vial for radioactivity counting.

In vitro IGF-1 bioactivity data (i.e., $EC_{50}$ values) for the compounds exemplified herein are also given in Table 2.

C) In Vitro Screening of IGF-1 Peptides for Insulin Receptor Cross Reactivity in U2OS Cells U2OS cells (Catalog #93-0466C3, DiscoveRX Corporation, Fremont, Calif., USA) were plated at $6 \times 10^5$ cells/mL in a 96-well poly-D-lysine plate 16 hours prior to assay in serum-free assay media. The wild-type insulin (Catalog #10908, Sigma, St. Louis, Mo., USA), the wild-type IGF-1 (Increlex®, Tercica, Inc., Brisbane, Calif., USA), or a test IGF-1 peptide disclosed in the instant application was added at a dose range of 10 μM (micromolar) to 0.15 nm (nanomolar), and incubated for 3 hours at 37° C. with 5% $CO_2$. PathHunter™ reagent (Catalog #93-001, DiscoveRX) was prepared according to manufacturer's instructions, and added to each well. Plates were incubated at room temperature for 1 hour. Luminescence was read on an Envision 2104 multi-label plate reader (PerkinElmer, Inc., Waltham, Mass., USA). Activity of each test peptide was analyzed and reported as maximum/minimum (max/min) values. In vitro insulin receptor cross reactivity data (i.e., max/min values) for the compounds exemplified herein are also given in Table 2.

Many of the compounds exemplified herein were found to be significantly more potent than the wild-type IGF-1 which has $IC_{50}$ value of 4.59 nM, $EC_{50}$ value of 3.75 nM, and the Max/Min value of 2.1.

TABLE 2

| Example Number | $IC_{50}$ (nM) | $EC_{50}$ (nM) | max/min |
|---|---|---|---|
| 1 | 0.57 | 0.51 | 2.1 |
| 2 | 0.50 | 2.31 | N/A |
| 3 | 2.41 | 7.17 | N/A |
| 4 | 0.88 | 1.90 | N/A |
| 5 | 1.14 | 1.89 | N/A |
| 6 | 0.66 | 0.98 | N/A |
| 7 | 4.11 | 7.41 | N/A |
| 8 | 19.02 | 32.00 | N/A |
| 9 | 3.62 | 8.31 | N/A |
| 10 | 2.90 | 1.09 | N/A |
| 11 | 1.85 | 3.34 | N/A |
| 12 | 1.47 | 5.11 | N/A |
| 13 | 1.25 | 7.02 | N/A |
| 14 | 5.94 | 3.56 | N/A |
| 15 | 0.81 | 3.70 | N/A |
| 16 | 2.61 | 7.59 | N/A |
| 17 | 2.77 | 4.59 | N/A |
| 18 | 0.72 | 3.33 | N/A |
| 19 | 2.77 | 7.69 | N/A |
| 20 | 1.60 | 3.13 | N/A |
| 21 | 1.57 | 3.95 | N/A |
| 22 | 0.91 | 4.22 | N/A |
| 23 | 2.69 | 3.86 | N/A |
| 24 | 2.89 | 2.60 | N/A |
| 25 | 2.40 | 6.72 | N/A |
| 26 | 3.60 | 1.28 | N/A |
| 27 | 0.58 | 1.13 | N/A |
| 28 | 3.25 | 2.12 | N/A |
| 29 | 13.25 | 4.86 | N/A |
| 30 | 1.95 | 1.87 | N/A |
| 31 | 2.03 | 1.18 | N/A |

TABLE 2-continued

| Example Number | $IC_{50}$ (nM) | $EC_{50}$ (nM) | max/min |
|---|---|---|---|
| 32 | 2.66 | 5.45 | N/A |
| 33 | 2.25 | 2.30 | N/A |
| 34 | N/A | N/A | N/A |
| 35 | 3.64 | 3.15 | N/A |
| 36 | N/A | N/A | N/A |
| 37 | 23.25 | 3.42 | N/A |
| 38 | 23.13 | 4.21 | N/A |
| 39 | 28.10 | 0.93 | N/A |
| 40 | N/A | N/A | N/A |
| 41 | N/A | N/A | N/A |
| 42 | 1.49 | 2.01 | N/A |
| 43 | 1.27 | 5.08 | N/A |
| 44 | 6.31 | 3.69 | N/A |
| 45 | 9.27 | 6.24 | N/A |
| 46 | N/A | N/A | N/A |
| 47 | 1.46 | 1.31 | N/A |
| 48 | 18.49 | 1.81 | N/A |
| 49 | 4.54 | 2.69 | N/A |
| 50 | 30.63 | 2.63 | N/A |
| 51 | 2.18 | 1.29 | N/A |
| 52 | 1.29 | 2.44 | N/A |
| 53 | N/A | N/A | N/A |
| 54 | 3.49 | 2.34 | N/A |

Administration

The analogues of IGF-1 of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids).

A typical method of making a salt of a peptide of the present invention is well known in the art and can be accomplished by standard methods of salt exchange. For instance, the TFA salt of a peptide of the present invention (the TFA salt results from the purification of the peptide by using preparative HPLC eluting with TFA containing buffer solutions) was converted into another salt, such as an acetate salt, by dissolving the peptide in a small amount of 0.25 N acetic acid aqueous solution. The resulting solution is applied to a Semi-Prep HPLC column (Zorbax, 300 SB, C-8). The column is eluted with (1) 0.1N ammonium acetate aqueous solution for 0.5 hours, (2) 0.25N acetic acid aqueous solution for 0.5 hours, and (3) a linear gradient (20% to 100% of solution B over 30 min) at a flow rate of 4 ml/min (solution A is a 0.25N acetic acid aqueous solution, and solution B is a 0.25N acetic acid in acetonitrile/water, with a 80:20 ratio). The fractions containing the peptide are collected and lyophilized to dryness.

The dosage of active ingredient in the compositions of this invention may be varied; however, it is necessary that the amount of the active ingredient be such that a suitable dosage form is obtained. The selected dosage depends on the desired therapeutic effect, on the route of administration, and on the duration of the treatment. Dosing is easily determined by the skilled, competent medical practitioner.

The compounds of this invention can be administered by oral, parenteral (e.g., intramuscular, intraperitoneal, intravenous or subcutaneous injection, or implant), nasal, vaginal, rectal, sublingual, or topical routes of administration, and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include, without limitation, pharmaceutically acceptable emulsions, solutions, suspensions, syrups, elixirs, and the like, containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include, without limitation, sterile aqueous or non-aqueous solutions, suspensions, emulsions, and the like. Examples of non-aqueous solvents or vehicles include propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. Preparations may be sterilized, for example, by filtration through a bacteria-retaining filter, by incorporating sterilizing agents into the compositions, by irradiating the compositions, and/or by heating the compositions. Pharmaceutical compositions containing the novel IGF-1 analogues described herein can also be manufactured in the form of sterile solid compositions which can be dissolved in sterile water or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents and patent applications. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. Pat. No. 5,821,221 teaches polymeric sustained release compositions comprising a bioactive agent and chitosan. U.S. Pat. No. 5,916,883 teaches sustained release compositions comprising a bioactive agent and cyclodextrin. PCT publication WO99/38536 teaches absorbable sustained release compositions of a bioactive agent. PCT publication WO00/04916 teaches a process for making microparticles comprising a therapeutic agent such as a peptide in an oil-in-water process. PCT publication WO00/09166 teaches complexes comprising a therapeutic agent such as a peptide and a phosphorylated polymer. PCT publication WO00/25826 teaches complexes comprising a therapeutic agent such as a peptide and a polymer bearing a non-polymerizable lactone.

Further, the invention disclosed in U.S. Pat. No. 7,258,864 features a method for treating a subject having insulin-like growth factor-1 deficiency (IGFD) comprising administering to a human pediatric subject an effective amount of the unmodified IGF-1 wherein the subject is characterized as follows: a) at the time of treatment or prior to initial treatment with IGF-1, has or had a height at least about 2 standard deviations (SD) below a normal mean for a corresponding age and gender, and b) at the time of treatment or prior to initial treatment with IGF-1, has or had a blood level of IGF-1 at least about −1 SD below normal mean levels wherein the subject does not have Laron syndrome or partial growth hormone insensitivity syndrome, and wherein said administering is effective to treat IGFD in the subject.

Similarly, the invention disclosed in WO 2006/130769 features a method for treating a subject having idiopathic short stature (ISS) comprising administering to a human pediatric subject suffering from ISS characterized by partial endogenous growth hormone activity or signaling, an amount of IGF-1 effective to promote growth in the subject, wherein the subject is further characterized as follows: a) at the time of treatment or prior to initial treatment with IGF-1, has or had a height at least about 2.0 standard deviations (SD) below the normal mean height for a subject of the same age and gender, and b) has blood levels of GH and IGF-1 that are at least normal for a subject of the same age and gender.

Further, the novel analogues disclosed herein are able to be administered alone or in combination with another therapeutic agent as determined by a skilled medical practitioner.

Unless defined otherwise, all technical and scientific terms used herein have the same meaning as commonly understood by one of ordinary skill in the art to which this invention belongs. Also, all publications, patent applications, patents and other references mentioned herein are hereby incorporated by reference, each in its entirety.

What is claimed is:

1. An analogue of IGF-1 according to Formula (I), $$H-A^{-1}-A^1-A^2-A^3-A^4-A^5-A^6-A^7-A^8-A^9-A^{10}-A^{11}-A^{12}-\\A^{13}-A^{14}-A^{15}-A^{16}-A^{17}-A^{18}-A^{19}-A^{20}-A^{21}-A^{22}-\\A^{23}-A^{24}-A^{25}-A^{26}-A^{27}-A^{28}-A^{29}-A^{30}-A^{31}-A^{32}-\\A^{33}-A^{34}-A^{35}-A^{36}-A^{37}-A^{38}-A^{39}-A^{40}-A^{41}-A^{42}-\\A^{43}-A^{44}-A^{45}-A^{46}-A^{47}-A^{48}-A^{49}-A^{50}-A^{51}-A^{52}-\\A^{53}-A^{54}-A^{55}-A^{56}-A^{57}-A^{58}-A^{59}-A^{60}-A^{61}-A^{62}-\\A^{63}-A^{64}-A^{65}-A^{66}-A^{67}-A^{68}-A^{69}-A^{70}-A^{71}-R^1, \quad (I)$$

wherein:
$A^{-1}$ is Ser or deleted;
$A^1$ is Gly or deleted;
$A^2$ is Pro-or deleted;
$A^3$ is Glu or deleted;
$A^4$ is Thr;
$A^5$ is Leu;
$A^6$ is Cys;
$A^7$ is Gly;
$A^8$ is Ala;
$A^9$ is Glu;
$A^{10}$ is Leu;
$A^{11}$ is Val;
$A^{12}$ is Asp;
$A^{13}$ is Ala;
$A^{14}$ is Leu;
$A^{15}$ is Gln;
$A^{16}$ is Phe;
$A^{17}$ is Val;
$A^{18}$ is Cys;
$A^{19}$ is Gly;
$A^{20}$ is Asp;
$A^{21}$ is Arg;
$A^{22}$ is Gly;
$A^{23}$ is Phe;

$A^{24}$ is Tyr;
$A^{25}$ is Phe;
$A^{26}$ is Asn;
$A^{27}$ is Lys or Pro;
$A^{28}$ is Pro or Lys;
$A^{29}$ is Thr;
$A^{30}$ is Gly;
$A^{31}$ is Tyr;
$A^{32}$ is Gly;
$A^{33}$ is Ser;
$A^{34}$ is Ser;
$A^{35}$ is Ser;
$A^{36}$ is Arg;
$A^{37}$ is Arg;
$A^{38}$ is Ala;
$A^{39}$ is Pro;
$A^{40}$ is Gln;
$A^{41}$ is Thr;
$A^{42}$ is Gly;
$A^{43}$ is Ile;
$A^{44}$ is Val;
$A^{45}$ is Asp;
$A^{46}$ is Glu;
$A^{47}$ is Cys;
$A^{48}$ is Cys;
$A^{49}$ is Phe or Thr;
$A^{50}$ is Arg or Ser;
$A^{51}$ is Ser;
$A^{52}$ is Cys;
$A^{53}$ is Asp or Ser;
$A^{54}$ is Leu;
$A^{55}$ is Arg or Tyr;
$A^{56}$ is Arg or Gln;
$A^{57}$ is Leu;
$A^{58}$ is Glu;
$A^{59}$ is Asn;
$A^{60}$ is Tyr or Phe;
$A^{61}$ is Cys;
$A^{62}$ is Ala or Asn;
$A^{63}$ is Pro, D-Pro, Thr or deleted;
$A^{64}$ is Leu, D-Leu, des-Leu or deleted;
$A^{65}$ is Lys, D-Lys, des-Lys or deleted;
$A^{66}$ is Pro, D-Pro or deleted;
$A^{67}$ is Ala, D-Ala or deleted;
$A^{68}$ is Lys, D-Lys or deleted;
$A^{69}$ is Ser, D-Ser or deleted;
$A^{70}$ is Ala, D-Ala, Glu or deleted; and
$A^{71}$ is deleted; and
$R^1$ is OH or $NH_2$;
provided that the side-chains of residue pairs $A^6$ and $A^{48}$, $A^{47}$ and $A^{52}$, and $A^{18}$ and $A^{61}$, each form a disulfide bond;
or a pharmaceutically acceptable salt thereof.

2. An analogue of IGF-1 according to claim 1, wherein said analogue is:
($Asn^{59}$)hIGF-1(1-70)-OH; (SEQ ID NO:1)
($Asn^{59}$)hIGF-1(1-62)-OH; (SEQ ID NO:2)
($Asn^{59}$)hIGF-1(4-70)-OH; (SEQ ID NO:3)
($Pro^{27}$, $Lys^{28}$, $Asn^{59}$)hIGF-1(1-70)-OH; (SEQ ID NO:4)
($Pro^{27}$, $Lys^{28}$, $Asn^{59}$)hIGF-1(1-62)-OH; (SEQ ID NO:5)
($Ser^{53}$, $Asn^{59}$)hIGF-1(1-70)-OH; (SEQ ID NO:6)
(Ser-$Gly^1$, $Asn^{59}$)hIGF-1(1-70)-OH; (SEQ ID NO:7)
($Asn^{59}$, $Thr^{63}$, des-$Leu^{64}$, des-$Lys^{65}$, $Glu^{70}$)hIGF-1(1-70)-OH; (SEQ ID NO:8)
($Tyr^{55}$, $Asn^{59}$)hIGF-1(1-70)-OH; (SEQ ID NO:9)
($Thr^{49}$, $Asn^{59}$)hIGF-1(1-70)-OH; (SEQ ID NO:10)
($Asn^{59, 62}$)hIGF-1(1-70)-OH; (SEQ ID NO:11)
($Asn^{59}$, $Phe^{60}$)hIGF-1(1-70)-OH; (SEQ ID NO:12)
($Ser^{50}$, $Asn^{59}$)hIGF-1(1-70)-OH; (SEQ ID NO:13)
($Gln^{56}$, $Asn^{59}$)hIGF-1(1-70)-OH; (SEQ ID NO:14)
($Asn^{59}$, D-$Pro^{63}$)hIGF-1(1-70)-OH;
($Asn^{59}$, D-$Leu^{64}$)hIGF-1(1-70)-OH;
($Asn^{59}$, D-$Lys^{65}$)hIGF-1(1-70)-OH;
($Asn^{59}$, D-$Pro^{66}$)hIGF-1(1-70)-OH;
($Asn^{59}$, D-$Ala^{67}$)hIGF-1(1-70)-OH;
($Asn^{59}$, D-$Lys^{68}$)hIGF-1(1-70)-OH;
($Asn^{59}$, D-$Ser^{69}$)hIGF-1(1-70)-OH; or
($Asn^{59}$, D-$Ala^{70}$)hIGF-1(1-70)-OH;
or a pharmaceutically acceptable salt thereof.

3. A pharmaceutical composition comprising a therapeutically effective amount of an analogue of claim 1 or a pharmaceutically acceptable salt thereof.

4. A method for treating conditions or diseases mediated by IGF-1 receptor binding, comprising the step of administering to a subject in need thereof a therapeutically effective amount of an analogue of claim 1 or a pharmaceutical composition of claim 3, wherein said condition or disease is selected from the group consisting of short stature, insulin resistance, diabetes and diabetic ketoacidosis.

5. The method of claim 4, wherein said subject in need of treating short stature is a human pediatric subject having insulin-like growth factor-1 deficiency (IGFD), wherein said administering is effective to treat IGFD in the human pediatric subject.

* * * * *